United States Patent
Campeau et al.

(10) Patent No.: US 11,607,405 B2
(45) Date of Patent: Mar. 21, 2023

(54) COMBINATION THERAPY FOR THE TREATMENT OF TRIPLE-NEGATIVE BREAST CANCER

(71) Applicant: ZENITH EPIGENETICS LTD., Calgary (CA)

(72) Inventors: Eric Campeau, Calgary (CA); Laura Tsujikawa, Calgary (CA); Sanjay Lakhotia, Orinda, CA (US)

(73) Assignee: Zenith Epigenetics Ltd., Calgary (CA)

( * ) Notice: Subject to any disclaimer, the term of this patent is extended or adjusted under 35 U.S.C. 154(b) by 124 days.

(21) Appl. No.: 17/275,458

(22) PCT Filed: Sep. 13, 2019

(86) PCT No.: PCT/IB2019/001009
§ 371 (c)(1),
(2) Date: Mar. 11, 2021

(87) PCT Pub. No.: WO2020/053655
PCT Pub. Date: Mar. 19, 2020

(65) Prior Publication Data
US 2022/0062246 A1    Mar. 3, 2022

Related U.S. Application Data

(60) Provisional application No. 62/730,879, filed on Sep. 13, 2018, provisional application No. 62/737,628, filed on Sep. 27, 2018.

(51) Int. Cl.
*A61K 31/437* (2006.01)
*A61K 31/5025* (2006.01)
*A61K 45/06* (2006.01)

(52) U.S. Cl.
CPC ........ *A61K 31/437* (2013.01); *A61K 31/5025* (2013.01); *A61K 45/06* (2013.01)

(58) Field of Classification Search
CPC .... A61K 31/437; A61K 31/5025; A61P 35/00
USPC ....................................................... 514/303
See application file for complete search history.

(56) References Cited

FOREIGN PATENT DOCUMENTS

WO    WO 2015/002754 A2 *  1/2015  ........... A61K 31/538
WO    WO 2017/015027 A1     1/2017

OTHER PUBLICATIONS

Sahni, J.M. et al.: Targeting bromodomain and extraterminal proteins in breast cancer. Pharmacol. Res., vol. 129, pp. 156-176, 2018.*
Ocana, A. et al., "BET Inhibitors as Novel Therapeutic Agents in Breast Cancer," *Oncotarget*, 2017, vol. 8, No. 41, Previously Presented. 71285-71291, Accepted: Jun. 28, 2017, Published: Aug. 1, 2017, Copyright Ocana et al., 7 pgs.
Roche, H. et al., "Poster Session 1: Clinical Studies—A Phase 3 Study of the Oral PARP Inhibitor Talazoparib (BMN 673) in BRCA Mutation Subjects with Advanced Breast Cancer (EMBRACA)," *Annals of Oncology 26* (Supplement 2), ii16-ii19, 2015, doi:10.1093/annonc/mdv090.1, Copyright The Author 2015, 1 pg.
Sahni, J.M., et al., "Targeting Bromodomain and Extraterminal Proteins in Breast Cancer," *HHS Public Access*, Author Manuscript, *Pharmacol Res.*, Mar. 2018, vol. 129, pp. 156-176, eeel1645, doi:10.1016/j.phrs.2017.11.015, 51 pgs.
Yang, L. et al., "Cancer—Repression of BET Activity Sensitizes Homologous Recombination-Proficient Cancers to PARP Inhibition," *Science Translational Medicine*, 9, eaal1645, Jul. 26, 2017— Research Article, Copyright 2017 The Authors, downloaded from Canadian Intellectual Property Office Resource Center on Jan. 3, 2020, 13 pgs.

* cited by examiner

*Primary Examiner* — Charanjit Aulakh
(74) *Attorney, Agent, or Firm* — Finnegan, Henderson, Farabow, Garrett & Dunner LLP

(57) ABSTRACT

The invention provides methods for treating triple negative breast cancer (TNBC), by co-administration of a BET bromodomain inhibitor selected from 1-benzyl-6-(3,5-dimethylisoxazol-4-yl)-N-methyl-1H-imidazo[4,5-b]pyridin-2-amine (Compound I), 1-benzyl-6-(3,5-dimethylisoxazol-4-yl)-1H-imidazo[4,5-b]pyridin-2-amine, and pharmaceutically acceptable salts/co-crystals thereof, and a second therapeutic agent to a subject in need thereof. The second therapeutic agent can be a PARP inhibitor, such as, e.g., talazoparib, olaparib or veliparib.

(Compound I)

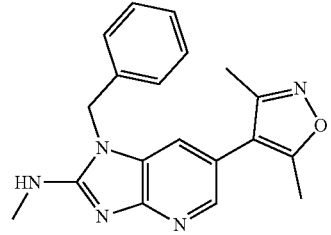

17 Claims, 12 Drawing Sheets

A)

B)

COMBINATION THERAPY FOR THE TREATMENT OF TRIPLE-NEGATIVE BREAST CANCER

This application is a U.S. national stage filing under 35 U.S.C. § 371 of International Application No. PCT/IB2019/001009, filed Sep. 13, 2019, which claims the benefit of priority of U.S. Provisional Application No. 62/730,879, filed Sep. 13, 2018, and U.S. Provisional Application No. 62/737,628, filed Sep. 27, 2018, all of which are incorporated herein by reference in their entirety.

The invention relates to the treatment of breast cancer.

BACKGROUND

Triple-negative breast cancer (TNBC), defined by the lack of expression of estrogen receptor ("ER") and progesterone receptor ("PR"), and the absence of human epidermal growth factor receptor 2 ("HER2") overexpression and amplification, represents about 10-20% of all breast cancers. TNBC patients have overall worse prognosis compared with other types of breast cancer with increased likelihood of early distance recurrences and death (Bauer et al. 2007). Metastatic disease is marked by a high rate of visceral and central nervous metastases with a median survival of approximately 1 year (Kassam et al. 2009). Novel therapeutic strategies are therefore highly needed.

Recent advances in the biology of the disease might offer opportunities with the classification of this heterogeneous entity into molecular subtypes with distinct drivers (Bareche et al. 2018). In particular, patients with breast cancer and germline BRCA1 and BRCA2 mutations derive benefit with treatment with a class of targeted agents called poly (ADP-ribose) polymerase (PARP) inhibitors that target base-excision repair (a mechanism of DNA repair) and that cause synthetic lethality in tumors with a deficit in a DNA repair mechanism such a homologous recombination. Indeed, two phase 3 trials that enrolled metastatic breast cancer patients with germline BRCA1 or BRCA2 mutations have reported positive results with PARP inhibitors Olaparib (Robson et al. 2017) and Talazoparib (Litton et al. 2017) versus standard chemotherapy. Following these results, the US FDA approved Olaparib for the treatment of germline BRCA-mutated metastatic breast cancer.

Even though the prevalence of BRCA1 and BRCA2 mutations is higher in TNBC (up to 24% in some cohorts) (Copson et al. 2018), the vast majority of patients with TNBC do not carry germline BRCA1 or BRCA2 mutations and would therefore not derive benefit from treatment with a PARP inhibitor (O'Shaughnessy et al. 2014).

In the preclinical setting, combinatorial strategies hold the promise of sensitizing BRCA-proficient tumors to PARP inhibitors and new data has been generated with some bromodomain and extra-terminal domain (BET) inhibitors. BET proteins are epigenetic readers and exhibit high selectivity for acetylated lysine residues in histones and other proteins. They function as transcription regulators via association with many gene promoters or enhancers. Early clinical trials with BET inhibitors (BETi) showed limited single-agent activity in patients with hematologic malignancies (Berthon et al. 2016), NUT carcinoma (Stathis et al. 2016) and very recently in solid tumors (Aftimos et al. 2017). However, there is promise for BETi in combinations with other agents as they modulate resistance mechanisms and confer sensitivity to various agents. Several explorative combination clinical trials are ongoing with BETi including combination with checkpoint monoclonal antibodies, androgen receptor antagonists, estrogen modulators, BCL2 inhibitors, and others.

However, at this time, it is unclear which, BET inhibitors will combine synergistically with a PARP inhibitor; what level of synergy is required; and which PARP inhibitor will be the best combination partner for each BET inhibitor, resulting in clinical benefit when administered to patients with TNBC. In addition to a clinical benefit, the combination also has to be safe and well tolerated at the efficacious doses. It cannot be predicted from the art which combinations will show the best overall profile.

SUMMARY

The present invention discloses methods of treating triple-negative breast cancer by co-administration of a BET bromodomain inhibitor of Formula Ia or Formula Ib, or a pharmaceutically acceptable salt or co-crystal thereof, and a second therapeutic agent to a subject in need thereof.

In some embodiments, the BET bromodomain inhibitor is administered simultaneously with the second therapeutic agent. In some embodiments, the BET bromodomain inhibitor is administered sequentially with the second therapeutic agent. In some embodiments, the BET bromodomain inhibitor is administered in a single pharmaceutical composition with the second therapeutic agent. In some embodiments, the BET bromodomain inhibitor and the second therapeutic agent are administered as separate compositions. In some embodiments, the BET bromodomain inhibitor and the second therapeutic agent are administered in combination with a checkpoint inhibitor.

In some embodiments the second therapeutic agent is an agent used to treat breast cancer. In some embodiments, the breast cancer is TNBC.

In some embodiments, the second therapeutic agent is a PARP inhibitor.

In some embodiments, the BET bromodomain inhibitor and the PARP inhibitor are administered in combination with a checkpoint inhibitor.

The BET bromodomain inhibitor used in the combination therapies of the invention is a compound of Formula Ia or Formula Ib

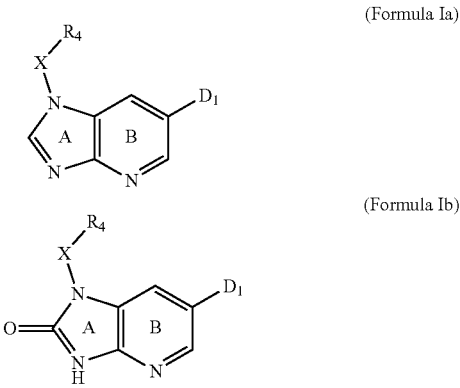

or a stereoisomer, tautomer, pharmaceutically acceptable salt, or co-crystal thereof, wherein:

Ring A and Ring B may be optionally substituted with groups independently selected from hydrogen, deuterium, —NH$_2$, amino, heterocycle (C$_4$-C$_6$), carbocycle (C$_4$-C$_6$), halogen, —CN, —OH, —CF$_3$, alkyl (C$_1$-C$_6$), thioalkyl (C$_1$-C$_6$), alkenyl (C$_2$-C$_6$), and alkoxy (C$_1$-C$_6$);

X is selected from —NH—, —CH$_2$—, —CH$_2$CH$_2$—, —CH$_2$CH$_2$CH$_2$—, —CH$_2$CH$_2$O—, —CH$_2$CH$_2$NH—, —CH$_2$CH$_2$S—, —C(O)—, —C(O)CH$_2$—, —C(O)CH$_2$CH$_2$—, —CH$_2$C(O)—, —CH$_2$CH$_2$C(O)—, —C(O)NH—, —C(O)O—, —C(O)S—, —C(O)NHCH$_2$—, —C(O)OCH$_2$—, —C(O)SCH$_2$—, wherein one or more hydrogen may independently be replaced with deuterium, hydroxyl, methyl, halogen, —CF$_3$, ketone, and where S may be oxidized to sulfoxide or sulfone;

R$_4$ is selected from optionally substituted 3-7 membered carbocycles and heterocycles; and D$_1$ is selected from the following 5-membered monocyclic heterocycles:

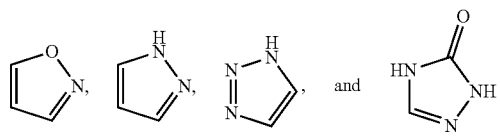

which are optionally substituted with deuterium, alkyl (C$_1$-C$_4$), alkoxy (C$_1$-C$_4$), amino, halogen, amide, —CF$_3$, —CN, —N$_3$, ketone (C$_1$-C$_4$), —S(O)Alkyl(C$_1$-C$_4$), —SO$_2$alkyl (C$_1$-C$_4$), -thioalkyl(C$_1$-C$_4$), —COOH, and/or ester, each of which may be optionally substituted with hydrogen, F, Cl, Br, —OH, —NH$_2$, —NHMe, —OMe, —SMe, oxo, and/or thio-oxo.

In some embodiments, the BET bromodomain inhibitor for use in the combination therapies of the invention is a compound of Formula Ia. In some embodiments, the compound of Formula Ia is 1-benzyl-6-(3,5-dimethylisoxazol-4-yl)-N-methyl-1H-imidazo[4,5-b]pyridine-2-amine ("Compound I"), which has the following formula:

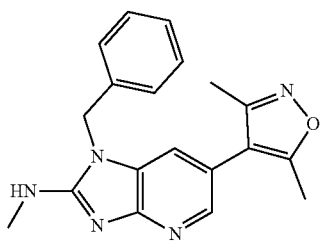

(Compound I)

In some embodiments, the BET bromodomain inhibitor of Formula Ia is a pharmaceutically acceptable salt or co-crystal of Compound I. In some embodiments, the BET bromodomain inhibitor is a mesylate salt/co-crystal of Compound I in crystalline form I.

DEFINITIONS

Figure 1:
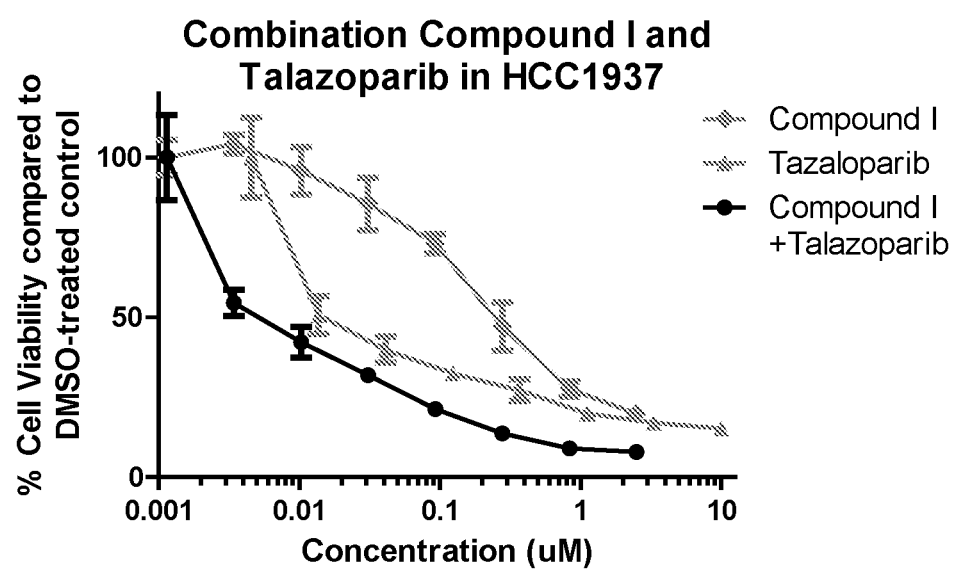
FIG. 1 shows the effect of Compound I, talazoparib, and the combination of Compound I and talazoparib on cell viability of TNBC HCC1937 cells (mutant BRCA1).

As used herein, "treatment" or "treating" refers to an amelioration of a disease or disorder, or at least one discernible symptom thereof. In another embodiment, "treatment" or "treating" refers to an amelioration of at least one measurable physical parameter, not necessarily discernible by the patient. In yet another embodiment, "treatment" or "treating" refers to inhibiting the progression of a disease or disorder, either physically, e.g., stabilization of a discernible symptom, physiologically, e.g., stabilization of a physical parameter, or both. In yet another embodiment, "treatment" or "treating" refers to delaying the onset of a disease or disorder.

By "optional" or "optionally" is meant that the subsequently described event or circumstance may or may not occur, and that the description includes instances where the event or circumstance occurs and instances in which is does not. For example, "optionally substituted aryl" encompasses both "aryl" and "substituted aryl" as defined below. It will be understood by those skilled in the art, with respect to any group containing one or more substituents, that such groups are not intended to introduce any substitution or substitution patterns that are sterically impractical, synthetically non-feasible and/or inherently unstable.

As used herein, the term "hydrate" refers to a crystal form with either a stoichiometric or non-stoichiometric amount of water is incorporated into the crystal structure.

The term "alkenyl" as used herein refers to an unsaturated straight or branched hydrocarbon having at least one carbon-carbon double bond, such as a straight or branched group of 2-8 carbon atoms, referred to herein as (C$_2$-C$_8$)alkenyl. Exemplary alkenyl groups include, but are not limited to, vinyl, allyl, butenyl, pentenyl, hexenyl, butadienyl, pentadienyl, hexadienyl, 2-ethylhexenyl, 2-propyl-2-butenyl, and 4-(2-methyl-3-butene)-pentenyl.

The term "alkoxy" as used herein refers to an alkyl group attached to an oxygen (—O-alkyl-). "Alkoxy" groups also include an alkenyl group attached to an oxygen ("alkenyloxy") or an alkynyl group attached to an oxygen ("alkynyloxy") groups. Exemplary alkoxy groups include, but are not limited to, groups with an alkyl, alkenyl or alkynyl group of 1-8 carbon atoms, referred to herein as $(C_1-C_8)$alkoxy. Exemplary alkoxy groups include, but are not limited to methoxy and ethoxy.

The term "alkyl" as used herein refers to a saturated straight or branched hydrocarbon, such as a straight or branched group of 1-8 carbon atoms, referred to herein as $(C_1-C_8)$alkyl. Exemplary alkyl groups include, but are not limited to, methyl, ethyl, propyl, isopropyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, butyl, isobutyl, t-butyl, pentyl, isopentyl, neopentyl, hexyl, heptyl, and octyl.

The term "amide" as used herein refers to —$NR_aC(O)(R_b)$—, or —$C(O)NR_bR_c$—, wherein $R_a$, $R_b$ and $R_c$ are each independently selected from alkyl, alkenyl, alkynyl, aryl, arylalkyl, cycloalkyl, haloalkyl, heteroaryl, heterocyclyl, and hydrogen. The amide can be attached to another group through the carbon, the nitrogen, $R_a$, $R_b$, or $R_c$. The amide also may be cyclic, for example $R_b$ and $R_c$, may be joined to form a 3- to 8-membered ring, such as 5- or 6-membered ring. The term "amide" encompasses groups such as sulfonamide, urea, ureido, carbamate, carbamic acid, and cyclic versions thereof. The term "amide" also encompasses an amide group attached to a carboxy group, e.g., -amide-COOH or salts such as -amide-COONa, an amino group attached to a carboxy group (e.g., -amino-COOH or salts such as -amino-COONa).

The term "amine" or "amino" as used herein refers to the form —$NR_dR_e$ or —$N(R_d)R_e$—, where $R_d$ and $R_e$ are independently selected from alkyl, alkenyl, alkynyl, aryl, arylalkyl, carbamate, cycloalkyl, haloalkyl, heteroaryl, heterocycle, and hydrogen. The amino can be attached to the parent molecular group through the nitrogen. The amino also may be cyclic, for example any two of $R_d$ and $R_e$ may be joined together or with the N to form a 3- to 12-membered ring (e.g., morpholino or piperidinyl). The term amino also includes the corresponding quaternary ammonium salt of any amino group. Exemplary amino groups include alkylamino groups, wherein at least one of $R_d$ or $R_e$ is an alkyl group. In some embodiments $R_d$ and $R_e$ each may be optionally substituted with hydroxyl, halogen, alkoxy, ester, or amino.

The term "aryl" as used herein refers to a mono-, bi-, or other multi-carbocyclic, aromatic ring system. The aryl group can optionally be fused to one or more rings selected from aryls, cycloalkyls, and heterocyclyls. The aryl groups of this present disclosure can be substituted with groups selected from alkoxy, aryloxy, alkyl, alkenyl, alkynyl, amide, amino, aryl, arylalkyl, carbamate, carboxy, cyano, cycloalkyl, ester, ether, formyl, halogen, haloalkyl, heteroaryl, heterocyclyl, hydroxyl, ketone, nitro, phosphate, sulfide, sulfinyl, sulfonyl, sulfonic acid, sulfonamide, and thioketone. Exemplary aryl groups include, but are not limited to, phenyl, tolyl, anthracenyl, fluorenyl, indenyl, azulenyl, and naphthyl, as well as benzo-fused carbocyclic moieties such as 5,6,7,8-tetrahydronaphthyl. Exemplary aryl groups also include, but are not limited to, a monocyclic aromatic ring system, wherein the ring comprises 6 carbon atoms, referred to herein as "$(C_6)$ aryl."

The term "arylalkyl" as used herein refers to an alkyl group having at least one aryl substituent (e.g., -aryl-alkyl-). Exemplary arylalkyl groups include, but are not limited to, arylalkyls having a monocyclic aromatic ring system, wherein the ring comprises 6 carbon atoms, referred to herein as "$(C_6)$ arylalkyl."

The term "carbamate" as used herein refers to the form —$R_gOC(O)N(R_h)$—, —$R_gOC(O)N(R_h)R_j$—, or —$OC(O)NR_hR_j$, wherein $R_g$, $R_h$ and $R_j$ are each independently selected from alkyl, alkenyl, alkynyl, aryl, arylalkyl, cycloalkyl, haloalkyl, heteroaryl, heterocyclyl, and hydrogen. Exemplary carbamates include, but are not limited to, arylcarbamates or heteroaryl carbamates (e.g., wherein at least one of $R_g$, $R_h$ and $R_j$ are independently selected from aryl or heteroaryl, such as pyridine, pyridazine, pyrimidine, and pyrazine).

The term "carbocycle" as used herein refers to an aryl or cycloalkyl group.

The term "carboxy" as used herein refers to —COOH or its corresponding carboxylate salts (e.g., —COONa). The term carboxy also includes "carboxycarbonyl," e.g. a carboxy group attached to a carbonyl group, e.g., —C(O)—COOH or salts, such as —C(O)—COONa.

The term "cycloalkoxy" as used herein refers to a cycloalkyl group attached to an oxygen.

The term "cycloalkyl" as used herein refers to a saturated or unsaturated cyclic, bicyclic, or bridged bicyclic hydrocarbon group of 3-12 carbons, or 3-8 carbons, referred to herein as "$(C_3-C_8)$cycloalkyl," derived from a cycloalkane. Exemplary cycloalkyl groups include, but are not limited to, cyclohexanes, cyclohexenes, cyclopentanes, and cyclopentenes. Cycloalkyl groups may be substituted with alkoxy, aryloxy, alkyl, alkenyl, alkynyl, amide, amino, aryl, arylalkyl, carbamate, carboxy, cyano, cycloalkyl, ester, ether, formyl, halogen, haloalkyl, heteroaryl, heterocyclyl, hydroxyl, ketone, nitro, phosphate, sulfide, sulfinyl, sulfonyl, sulfonic acid, sulfonamide and thioketone. Cycloalkyl groups can be fused to other cycloalkyl saturated or unsaturated, aryl, or heterocyclyl groups.

The term "dicarboxylic acid" as used herein refers to a group containing at least two carboxylic acid groups such as saturated and unsaturated hydrocarbon dicarboxylic acids and salts thereof. Exemplary dicarboxylic acids include alkyl dicarboxylic acids. Dicarboxylic acids may be substituted with alkoxy, aryloxy, alkyl, alkenyl, alkynyl, amide, amino, aryl, arylalkyl, carbamate, carboxy, cyano, cycloalkyl, ester, ether, formyl, halogen, haloalkyl, heteroaryl, heterocyclyl, hydrogen, hydroxyl, ketone, nitro, phosphate, sulfide, sulfinyl, sulfonyl, sulfonic acid, sulfonamide and thioketone. Dicarboxylic acids include, but are not limited to succinic acid, glutaric acid, adipic acid, suberic acid, sebacic acid, azelaic acid, maleic acid, phthalic acid, aspartic acid, glutamic acid, malonic acid, fumaric acid, (+)/(−)-malic acid, (+)/(−) tartaric acid, isophthalic acid, and terephthalic acid. Dicarboxylic acids further include carboxylic acid derivatives thereof, such as anhydrides, imides, hydrazides (for example, succinic anhydride and succinimide).

The term "ester" refers to the structure —C(O)O—, —C(O)O—$R_j$—, —$R_kC(O)O$—$R_j$—, or —$R_kC(O)O$—, where O is not bound to hydrogen, and $R_j$ and $R_k$ can independently be selected from alkoxy, aryloxy, alkyl, alkenyl, alkynyl, amide, amino, aryl, arylalkyl, cycloalkyl, ether, haloalkyl, heteroaryl, and heterocyclyl. $R_k$ can be a hydrogen, but $R_j$ cannot be hydrogen. The ester may be cyclic, for example the carbon atom and $R_j$, the oxygen atom and $R_k$, or $R_j$ and $R_k$ may be joined to form a 3- to 12-membered ring. Exemplary esters include, but are not limited to, alkyl esters wherein at least one of $R_j$ or $R_k$ is alkyl, such as —O—C(O)-alkyl, —C(O)—O-alkyl-, and -alkyl-C(O)—O-alkyl-. Exemplary esters also include aryl or heteroaryl esters, e.g. wherein at least one of $R_j$ or $R_k$ is a heteroaryl group such as pyridine, pyridazine, pyrimidine and pyrazine, such as a nicotinate ester. Exemplary esters also include reverse esters having the structure —$R_k$C(O)O—, where the oxygen is bound to the parent molecule. Exemplary reverse esters include succinate, D-argininate, L-argininate, L-lysinate and D-lysinate. Esters also include carboxylic acid anhydrides and acid halides.

The terms "halo" or "halogen" as used herein refer to F, Cl, Br, or I.

The term "haloalkyl" as used herein refers to an alkyl group substituted with one or more halogen atoms. "Haloalkyls" also encompass alkenyl or alkynyl groups substituted with one or more halogen atoms.

The term "heteroaryl" as used herein refers to a mono-, bi-, or multi-cyclic, aromatic ring system containing one or more heteroatoms, for example 1-3 heteroatoms, such as nitrogen, oxygen, and sulfur. Heteroaryls can be substituted with one or more substituents including alkoxy, aryloxy, alkyl, alkenyl, alkynyl, amide, amino, aryl, arylalkyl, carbamate, carboxy, cyano, cycloalkyl, ester, ether, formyl, halogen, haloalkyl, heteroaryl, heterocyclyl, hydroxyl, ketone, nitro, phosphate, sulfide, sulfinyl, sulfonyl, sulfonic acid, sulfonamide and thioketone. Heteroaryls can also be fused to non-aromatic rings. Illustrative examples of heteroaryl groups include, but are not limited to, pyridinyl, pyridazinyl, pyrimidyl, pyrazyl, triazinyl, pyrrolyl, pyrazolyl, imidazolyl, (1,2,3)- and (1,2,4)-triazolyl, pyrazinyl, pyrimidilyl, tetrazolyl, furyl, thienyl, isoxazolyl, thiazolyl, furyl, phenyl, isoxazolyl, and oxazolyl. Exemplary heteroaryl groups include, but are not limited to, a monocyclic aromatic ring, wherein the ring comprises 2-5 carbon atoms and 1-3 heteroatoms, referred to herein as "($C_2$-$C_5$) heteroaryl."

The terms "heterocycle," "heterocyclyl," or "heterocyclic" as used herein refer to a saturated or unsaturated 3-, 4-, 5-, 6- or 7-membered ring containing one, two, or three heteroatoms independently selected from nitrogen, oxygen, and sulfur. Heterocycles can be aromatic (heteroaryls) or non-aromatic. Heterocycles can be substituted with one or more substituents including alkoxy, aryloxy, alkyl, alkenyl, alkynyl, amide, amino, aryl, arylalkyl, carbamate, carboxy, cyano, cycloalkyl, ester, ether, formyl, halogen, haloalkyl, heteroaryl, heterocyclyl, hydroxyl, ketone, nitro, phosphate, sulfide, sulfinyl, sulfonyl, sulfonic acid, sulfonamide and thioketone. Heterocycles also include bicyclic, tricyclic, and tetracyclic groups in which any of the above heterocyclic rings is fused to one or two rings independently selected from aryls, cycloalkyls, and heterocycles. Exemplary heterocycles include acridinyl, benzimidazolyl, benzofuryl, benzothiazolyl, benzothienyl, benzoxazolyl, biotinyl, cinnolinyl, dihydrofuryl, dihydroindolyl, dihydropyranyl, dihydrothienyl, dithiazolyl, furyl, homopiperidinyl, imidazolidinyl, imidazolinyl, imidazolyl, indolyl, isoquinolyl, isothiazolidinyl, isothiazolyl, isoxazolidinyl, isoxazolyl, morpholinyl, oxadiazolyl, oxazolidinyl, oxazolyl, piperazinyl, piperidinyl, pyranyl, pyrazolidinyl, pyrazinyl, pyrazolyl, pyrazolinyl, pyridazinyl, pyridyl, pyrimidinyl, pyrimidyl, pyrrolidinyl, pyrrolidin-2-onyl, pyrrolinyl, pyrrolyl, quinolinyl, quinoxaloyl, tetrahydrofuryl, tetrahydroisoquinolyl, tetrahydropyranyl, tetrahydroquinolyl, tetrazolyl, thiadiazolyl, thiazolidinyl, thiazolyl, thienyl, thiomorpholinyl, thiopyranyl, and triazolyl.

The terms "hydroxy" and "hydroxyl" as used herein refer to —OH.

The term "hydroxyalkyl" as used herein refers to a hydroxy attached to an alkyl group.

The term "hydroxyaryl" as used herein refers to a hydroxy attached to an aryl group.

The term "ketone" as used herein refers to the structure —C(O)—Rn (such as acetyl, —C(O)CH$_3$) or —$R_n$—C(O)—$R_o$. The ketone can be attached to another group through $R_n$ or $R_o$. $R_n$ or $R_o$ can be alkyl, alkenyl, alkynyl, cycloalkyl, heterocyclyl or aryl, or $R_n$ or $R_o$ can be joined to form a 3- to 12-membered ring.

The term "phenyl" as used herein refers to a 6-membered carbocyclic aromatic ring. The phenyl group can also be fused to a cyclohexane or cyclopentane ring. Phenyl can be substituted with one or more substituents including alkoxy, aryloxy, alkyl, alkenyl, alkynyl, amide, amino, aryl, arylalkyl, carbamate, carboxy, cyano, cycloalkyl, ester, ether, formyl, halogen, haloalkyl, heteroaryl, heterocyclyl, hydroxyl, ketone, phosphate, sulfide, sulfinyl, sulfonyl, sulfonic acid, sulfonamide and thioketone.

The term "thioalkyl" as used herein refers to an alkyl group attached to a sulfur (—S-alkyl-).

"Alkyl," "alkenyl," "alkynyl", "alkoxy", "amino" and "amide" groups can be optionally substituted with or interrupted by or branched with at least one group selected from alkoxy, aryloxy, alkyl, alkenyl, alkynyl, amide, amino, aryl, arylalkyl, carbamate, carbonyl, carboxy, cyano, cycloalkyl, ester, ether, formyl, halogen, haloalkyl, heteroaryl, heterocyclyl, hydroxyl, ketone, phosphate, sulfide, sulfinyl, sulfonyl, sulfonic acid, sulfonamide, thioketone, ureido and N. The substituents may be branched to form a substituted or unsubstituted heterocycle or cycloalkyl.

As used herein, a suitable substitution on an optionally substituted substituent refers to a group that does not nullify the synthetic or pharmaceutical utility of the compounds of the present disclosure or the intermediates useful for preparing them. Examples of suitable substitutions include, but are not limited to: $C_{1-8}$ alkyl, alkenyl or alkynyl; $C_{1-6}$ aryl, $C_{2-5}$ heteroaryl; $C_{37}$ cycloalkyl; $C_{1-8}$ alkoxy; $C_6$ aryloxy; —CN; —OH; oxo; halo, carboxy; amino, such as —NH($C_{1-8}$ alkyl), —N($C_{1-8}$ alkyl)$_2$, —NH(($C_6$)aryl), or —N(($C_6$) aryl)$_2$; formyl; ketones, such as —CO($C_{1-8}$ alkyl), —CO(($C_6$ aryl)$_2$; esters, such as —CO$_2$($C_{1-8}$ alkyl) and —CO$_2$ ($C_6$ aryl). One of skill in art can readily choose a suitable substitution based on the stability and pharmacological and synthetic activity of the compound of the present disclosure.

The term "pharmaceutically acceptable composition" as used herein refers to a composition comprising at least one compound as disclosed herein formulated together with one or more pharmaceutically acceptable carriers.

The term "pharmaceutically acceptable carrier" as used herein refers to any and all solvents, dispersion media, coatings, isotonic and absorption delaying agents, and the like, that are compatible with pharmaceutical administration. The use of such media and agents for pharmaceutically active substances is well known in the art. The compositions may also contain other active compounds providing supplemental, additional, or enhanced therapeutic functions.

The term "triple negative breast cancer" or "TNBC" is used herein to refer to breast cancer that is characterized by tumors with less than 10% of the cells positive for estrogen receptor and progesterone receptor and without HER2 amplification as well as patients who are not candidates for endocrine therapy (Dawood 2010). TNBC tends to be more aggressive than other types of breast cancer and thus, is more likely to spread beyond the breast and/or to recur after treatment.

The term "immunotherapy agent" is used herein to refer to agents used for treatment of disease by activating or suppressing the immune system.

The term "checkpoint inhibitor" is used herein to refer to therapeutic agents that target immune checkpoints.

EXEMPLARY EMBODIMENTS OF THE INVENTION

As summarized above, the invention provides methods of treating TNBC with a combination therapy that includes administration of a BET bromodomain inhibitor of Formula Ia or Formula Ib, or a pharmaceutically acceptable salt or co-crystal thereof, and a second therapeutic agent to a subject in need thereof.

In one embodiment, the invention provides a method for treating TNBC comprising administrating a BET bromodomain inhibitor of Formula Ia or Formula Ib

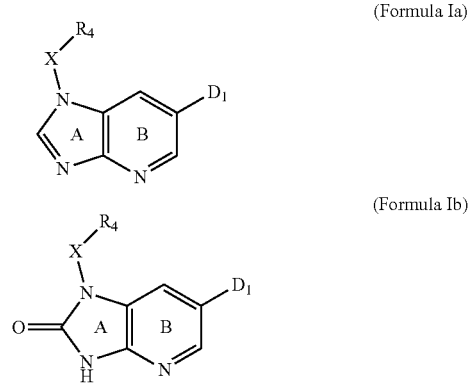

or a stereoisomer, tautomer, pharmaceutically acceptable salt, or co-crystal, or hydrate thereof, together with a second therapeutic agent, wherein:

Ring A and Ring B may be optionally substituted with groups independently selected from hydrogen, deuterium, —$NH_2$, amino, heterocycle($C_4$-$C_6$), carbocycle ($C_4$-$C_6$), halogen, —CN, —OH, —$CF_3$, alkyl ($C_1$-$C_6$), thioalkyl ($C_1$-$C_6$), alkenyl ($C_1$-$C_6$), and alkoxy ($C_1$-$C_6$);

X is selected from —NH—, —$CH_2$—, —$CH_2CH_2$—, —$CH_2CH_2CH_2$—, —$CH_2CH_2O$—, —$CH_2CH_2NH$—, —$CH_2CH_2S$—, —C(O)—, —C(O)$CH_2$—, —C(O)$CH_2CH_2$—, —$CH_2C$(O)—, —$CH_2CH_2C$(O)—, —C(O)NH—, —C(O)O—, —C(O)S—, —C(O)NH$CH_2$—, —C(O)O$CH_2$—, —C(O)S$CH_2$—, wherein one or more hydrogen may independently be replaced with deuterium, hydroxyl, methyl, halogen, —$CF_3$, ketone, and where S may be oxidized to sulfoxide or sulfone;

$R_4$ is selected from optionally substituted 3-7 membered carbocycles and heterocycles; and $D_1$ is selected from the following 5-membered monocyclic heterocycles:

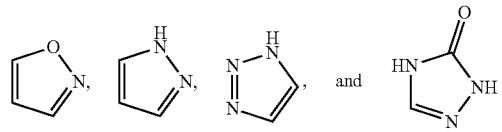

which are optionally substituted with hydrogen, deuterium, alkyl ($C_1$-$C_4$), alkoxy ($C_1$-$C_4$), amino, halogen, amide, —$CF_3$, —CN, —$N_3$, ketone ($C_1$-$C_4$), —S(O)Alkyl($C_1$-$C_4$), —$SO_2$alkyl($C_1$-$C_4$), -thioalkyl($C_1$-$C_4$), —COOH, and/or ester, each of which may be optionally substituted with hydrogen, F, Cl, Br, —OH, —$NH_2$, —NHMe, —OMe, —SMe, oxo, and/or thio-oxo.

Compounds of Formula Ia and Ib, including Compound I, have been previously described in International Patent Publication WO 2015/002754, incorporated herein by reference in its entirety, and particularly for its description of the compounds of Formula Ia and Formula Ib, including Compound I, their synthesis, and the demonstration of their BET bromodomain inhibitor activity.

In some embodiments, the BET bromodomain inhibitor of Formula Ia or Formula Ib is selected from:
1-Benzyl-6-(3,5-dimethylisoxazol-4-yl)-N-ethyl-1H-imidazo[4,5-b]pyridin-2-amine;
1-Benzyl-6-(3,5-dimethylisoxazol-4-yl)-N-methyl-1H-imidazo[4,5-b]pyridin-2-amine;
N,1-Dibenzyl-6-(3,5-dimethylisoxazol-4-yl)-1H-imidazo[4,5-b]pyridin-2-amine;
1-Benzyl-6-(3,5-dimethylisoxazol-4-yl)-N-(pyridin-3-ylmethyl)-1H-imidazo[4,5-b]pyridin-2-amine;
4-(1-Benzyl-2-(pyrrolidin-1-yl)-1H-imidazo[4,5-b]pyridin-6-yl)-3,5-dimethylisoxazole;
4-(2-(Azetidin-1-yl)-1-(cyclopentylmethyl)-1H-imidazo[4,5-b]pyridin-6-yl)-3,5-dimethylisoxazole;
1-Benzyl-6-(3,5-dimethylisoxazol-4-yl)-1H-imidazo[4,5-b]pyridin-2-amine;
1-(cyclopentylmethyl)-6-(3,5-dimethylisoxazol-4-yl)-N-(tetrahydro-2H-pyran-4-yl)-1H-imidazo[4,5-b]pyridin-2-amine;
4-Amino-1-benzyl-6-(3,5-dimethylisoxazol-4-yl)-1H-benzo[d]imidazol-2(3H)-one;
4-Amino-6-(3,5-dimethylisoxazol-4-yl)-1-(4-methoxybenzyl)-1H-benzo[d]imidazol-2(3H)-one;
4-Amino-6-(3,5-dimethylisoxazol-4-yl)-1-(1-phenylethyl)-1H-benzo[d]imidazol-2(3H)-one;
4-Amino-1-benzyl-6-(3,5-dimethylisoxazol-4-yl)-3-methyl-1H-benzo[d]imidazol-2(3H)-one;
or a pharmaceutically acceptable salt or co-crystal thereof.

In some embodiments, the invention provides a method for treating TMBC comprising administrating to a subject in need thereof, a BET bromodomain inhibitor selected from 1-benzyl-6-(3,5-dimethylisoxazol-4-yl)-N-methyl-1H-imidazo[4,5-b]pyridin-2-amine (Compound I), 1-benzyl-6-(3,5-dimethylisoxazol-4-yl)-1H-imidazo[4,5-b]pyridin-2-amine, and pharmaceutically acceptable salts or co-crystals thereof, concomitantly with another therapeutic agent.

In one embodiment, the second therapeutic agent is a PARP inhibitor. In some embodiments, the PARP inhibitor is selected from olaparib, talazoparib, rucaparib, veliparib, niraparib, pamiparib, CEP9722, and E7016.

In one embodiment, the second therapeutic agent is olaparib.

In one embodiment, the second therapeutic agent is talazoparib.

In one embodiment, the subject has previously been treated with a breast cancer therapy.

In one embodiment, the subject has previously been treated with chemotherapy.

In one embodiment, the subject has previously been treated with a PARP inhibitor.

In one embodiment, the subject has been previously treated with a PARP inhibitor in combination with an immunotherapy agent.

In one embodiment, the subject has been previously treated with a PARP combination with a checkpoint inhibitor.

In one embodiment, the subject has previously shown disease progression on treatment with a PARP inhibitor.

In one embodiment, the subject has previously shown disease progression on treatment with a PARP inhibitor in combination with an immunotherapy agent.

In one embodiment, the subject has previously been treated with a combination therapy containing abraxane as one of the therapeutics agents.

In one embodiment, the subject has previously been treated with immunotherapy.

In one embodiment, the subject has previously shown disease progression on treatment with immunotherapy.

In one embodiment, the subject showed no evidence of disease progression during platinum treatment either in the neoadjuvant or in the metastatic setting. For subjects receiving platinum in the neoadjuvant setting, at least 12 months must have elapsed between the last dose of platinum-based treatment and enrollment.

In one embodiment, the subject has previously been treated with combination therapy containing Tecentriq as one of the therapeutics agents.

In one embodiment, the BET bromodomain inhibitor is a pharmaceutically acceptable salt or co-crystal of Compound I. In one embodiment, the BET bromodomain inhibitor is the mesylate salt or co-crystal of Compound I.

In one embodiment, the subject is a human.

In one embodiment, the subject with breast cancer has one or both germline mutations BRCA1 and BRCA2.

In one embodiment, the subject with TNBC has one or both germline mutations BRCA1 and BRCA2.

In one embodiment, the subject with breast cancer does not carry germline mutations to BRCA1 or BRCA2.

In one embodiment, the subject with TNBC does not carry germline mutations to BRCA1 or BRCA2.

In one embodiment, the subject with breast cancer has somatic mutations to BRCA1 and BRCA2.

In one embodiment, the subject with TNBC has somatic mutations to BRCA1 and BRCA2.

In one embodiment, the subject with breast cancer has somatic mutations to either BRCA1 or BRCA2.

In one embodiment, the subject with TNBC has somatic mutations to either BRCA1 or BRCA2.

In one embodiment, the subject with breast cancer has mutations or alterations that affect BRCA1 and or BRCA2 gene expression, including methylation of the promoter of the BRCA1 or BRCA2 gene that prevents its expression.

In one embodiment, the subject with TNBC has mutations or alterations that affect BRCA1 and or BRCA2 gene expression, including methylation of the promoter of the BRCA1 or BRCA2 gene that prevents its expression.

In one embodiment, the subject with breast cancer has one or more somatic mutations to homologous recombination (HR) or non-homologous end-joining (NHEJ) genes, including ATM, CHEK2, NBN, PALB2, ATR, RAD51, RAD54, DSS1, RPA1, CHK1, FANCD2, FANCA, FANCC, FANCM, BARD1, RAD51C, RAD51D, RIF1, and BRIP1.

In one embodiment, the subject with TNBC has one or more somatic mutations to homologous recombination (HR) or non-homologous end-joining (NHEJ) genes, including ATM, CHEK2, NBN, PALB2, ATR, RAD51, RAD54, DSS1, RPA1, CHK1, FANCD2, FANCA, FANCC, FANCM, BARD1, RAD51C, RAD51D, RIF1, and BRIP1.

In one embodiment, the subject with breast cancer has one or more germline mutations to homologous recombination (HR) genes or non-homologous end-joining (NHEJ), including ATM, CHEK2, NBN, PALB2, ATR, RAD51, RAD54, DSS1, RPA1, CHK1, FANCD2, FANCA, FANCC, FANCM, BARD1, RAD51C, RAD51D, RIF1, and BRIP1.

In one embodiment, the subject with TNBC has one or more germline mutations to homologous recombination (HR) or on-homologous end-joining (NHEJ) genes, including ATM, CHEK2, NBN, PALB2, ATR, RAD51, RAD54, DSS1, RPA1, CHK1, FANCD2, FANCA, FANCC, FANCM, BARD1, RAD51C, RAD51D, RIF1, and BRIP1.

In one embodiment, the subject has a tumor characterized as homologous recombination (HR)-proficient.

In one embodiment, the subject has a tumor characterized as homologous recombination deficient (HRD).

In one embodiment, a compound selected from 1-benzyl-6-(3,5-dimethylisoxazol-4-yl)-N-methyl-1H-imidazo[4,5-b]pyridin-2-amine (Compound I), 1-benzyl-6-(3,5-dimethylisoxazol-4-yl)-1H-imidazo[4,5-b]pyridin-2-amine and pharmaceutically acceptable salts or co-crystals thereof, is dosed with a PARP inhibitor without resulting in dose-limiting thrombocytopenia.

In one embodiment, a compound selected from 1-benzyl-6-(3,5-dimethylisoxazol-4-yl)-N-methyl-1H-imidazo[4,5-b]pyridin-2-amine (Compound I) and 1-benzyl-6-(3,5-dimethylisoxazol-4-yl)-1H-imidazo[4,5-b]pyridin-2-amine and pharmaceutically acceptable salts or co-crystals thereof, is dosed with talazoparib without resulting in thrombocytopenia as a dose-limiting toxicity.

In one embodiment, the BET bromodomain inhibitor as described herein may be administered concomitantly with the other therapeutic agent. Concomitantly means that the BET bromodomain inhibitor as described herein and the other therapeutic agent are administered with a time separation of a few seconds (for example 15 sec., 30 sec., 45 sec., 60 sec. or less), several minutes (for example 1 min., 2 min., 5 min. or less, 10 min. or less, 15 min. or less), or 1-12 hours. When administered concomitantly, the BET bromodomain inhibitor and the other therapeutic agent may be administered in two or more administrations, and contained in separate compositions or dosage forms, which may be contained in the same or different package or packages.

In one embodiment, the BET bromodomain inhibitor as described herein and the PARP inhibitor (PARPi) may be administered on the same or different schedules.

In one embodiment, Compound I as described herein and talazoparib may be administered on the same or different schedules, including:

Compound I—continuously+PARPi—continuously

Compound I—3 weeks on, one week off+PARPi—continuously;

Compound I—2 weeks on, two weeks off+PARPi—continuously;

Compound I—3 weeks on, one week off+PARPi—3 weeks on, one week off;

Compound I—2 weeks on, two weeks off+PARPi—3 weeks on, one week off;

Compound I—continuously+PARPi—3 weeks on, one week off; or

Compound I—continuously+PARPi—2 weeks on, two weeks off.

In certain embodiments, a compound selected from Compound I and 1-benzyl-6-(3,5-dimethylisoxazol-4-yl)-1H-imidazo[4,5-b]pyridin-2-amine for use in the combination therapies of the invention, is dosed at 25 to 200 mg/day. In some embodiments the compound selected from Compound I and 1-benzyl-6-(3,5-dimethylisoxazol-4-yl)-1H-imidazo[4,5-b]pyridin-2-amine is administered to a subject at a dose of 36 to 144 mg/day. In some embodiments, the compound selected from Compound I and 1-benzyl-6-(3,5-dimethylisoxazol-4-yl)-1H-imidazo[4,5-b]pyridin-2-amine for use in the combination therapies of the invention is administered to a subject at a dose of 48 mg to 96 mg/day. In some embodiments, the compound selected from Compound I and 1-benzyl-6-(3,5-dimethylisoxazol-4-yl)-1H-imidazo[4,5-b]pyridin-2-amine for use in the combination therapies of the invention is administered to a subject at a dose of 48 mg, 60 mg, 72 mg, or 96 mg/day. In any of the embodiments described herein, the compound selected from Compound I and 1-benzyl-6-(3,5-dimethylisoxazol-4-yl)-1H-imidazo[4,5-b]pyridin-2-amine may be administered in combination with 0.25 mg to 1 mg of talazoparib. In some embodiments, 36 to 144 mg of Compound I is administered in combination with 0.25 to 1 mg of talazoparib.

In certain embodiments, a compound selected from pharmaceutically acceptable salts or co crystals of Compound I and 1-benzyl-6-(3,5-dimethylisoxazol-4-yl)-1H-imidazo[4,5-b]pyridin-2-amine may be administered in the combination therapies of the invention at a dosage level providing an exposure in humans similar to an amount of 25 to 200 mg/day of the corresponding free base. In certain embodiments, the compound selected from pharmaceutically acceptable salts or co crystals of Compound I and 1-benzyl-6-(3,5-dimethylisoxazol-4-yl)-1H-imidazo[4,5-b]pyridin-2-amine may be administered in the combination therapies of the invention at a dosage level providing an exposure in humans similar to an amount of 36 to 144 mg/day of the corresponding free base. In certain embodiments, a compound selected from pharmaceutically acceptable salts or co crystals of Compound I and 1-benzyl-6-(3,5-dimethylisoxazol-4-yl)-1H-imidazo[4,5-b]pyridin-2-amine may be administered in the combination therapies of the invention at a dosage level providing an exposure in humans similar to an amount of 48 mg to 96 mg/day of the corresponding free base. In any of the embodiments described herein, the compound selected from pharmaceutically acceptable salts or co crystals of Compound I and 1-benzyl-6-(3,5-dimethylisoxazol-4-yl)-1H-imidazo[4,5-b]pyridin-2-amine may be administered in combination with 0.25 mg to 1 mg of talazoparib.

REFERENCES

Aftimos P, Bechter O, Awada A, Jungels C, Dumez H, Huyvaert N, Costermans J, Lee C, Meeus M A, Burkard U, Musa H, Zhao Y, Schoffski P. Phase I first-in-man trial of a novel bromodomain and extra-terminal domain (BET) inhibitor (BI 894999) in patients (Pts) with advanced solid tumors. J Clin Oncol 35, 2017 (suppl; abstr 2504)

Bareche Y, Venet D, Ignatiadis M, Aftimos P, Piccart M, Rothe F, Sotiriou C. Unravelling triple-negative breast cancer molecular heterogeneity using an integrative multiomic analysis. Ann Oncol. 2018 Jan. 22

Bauer, K R, Brown M, Cress R D, Parise C A, Caggiano V. Descriptive analysis of estrogen receptor (ER) negative, progesterone receptor (PR)-negative, and HER2-negative invasive breast cancer, the so-called triple-negative phenotype: a population-based study from the California cancer Registry. Cancer. 2007 May 1; 109(9):1721-8

Berthon C, Raffoux E, Thomas X, Vey N, Gomez-Roca C, Yee K, Taussig D C, Rezai K, Roumier C, Herait P, Kahatt C, Quesnel B, Michallet M, Recher C, Lokiec F, Preudhomme C, Dombret H. Bromodomain inhibitor OTX015 in patients with acute leukaemia: a dose-escalation, phase 1 study. Lancet Haematol. 2016 April; 3(4):e186-95

Copson E R, Maishman T C, Tapper W J, Cutress R I, Greville-Heygate S, Altman D G, Eccles B, Gerty S, Durcan L T, Jones L, Evans D G, Thompson A M, Pharoah P, Easton D F, Dunning A M, Hanby A, Lakhani S, Eeles R, Gilbert F J, Hamed H, Hodgson S, Simmonds P, Stanton L, Eccles D M. Germline BRCA mutation and outcome in young-onset breast cancer (POSH): a prospective cohort study. Lancet Oncol. 2018 February; 19(2): 169-180. doi: 10.1016/S1470-2045(17)30891-4

Dawood S, Triple-Negative Breast Cancer. Drugs (2010) 70(17):2247-2258

Kassam F, Enright K, Dent R, Dranitsaris G, Myers J, Flynn C, Fralick M, Kumar R, Clemons M. Survival outcomes for patients with metastatic triple-negative breast cancer: implications for clinical practice and trial design. Clin Breast Cancer. 2009 February; 9(1):29-33

Litton J, Rugo H S, Ettl J, Hurvitz S, Gongalves A, Lee K-H, Fehrenbacher L, Yerushalmi R, Mina L A, Martin M, Roché H, Im Y-H, Quek R G W, Tudor I C, Hannah A L, Eiermann W, Blum J L. EMBRACA: A phase 3 trial comparing talazoparib, an oral PARP inhibitor, to physician's choice of therapy in patients with advanced breast cancer and a germline BRCAmutation [abstract]. In: Proceedings of the 2017 San Antonio Breast Cancer Symposium; 2017 Dec. 5-9; San Antonio, Tex. Philadelphia (Pa.): AACR; Cancer Res 2018; 78(4 Suppl):Abstract nr GS6-07

O'Shaughnessy J, Schwartzberg L, Danso M A, Miller K D, Rugo H S, Neubauer M, Robert N, Hellerstedt B, Saleh M, Richards P, Specht J M, Yardley D A, Carlson R W, Finn R S, Charpentier E, Garcia-Ribas I, Winer E P. Phase 11 study of iniparib plus gemcitabine and carboplatin versus gemcitabine and carboplatin in patients with metastatic triple-negative breast cancer. J Clin Oncol. 2014 Dec. 1; 32(34):3840-7

Robson M, Im S A, Senkus E, Xu B, Domchek S M, Masuda N, Delaloge S, Li W, Tung N, Armstrong A, Wu W, Goessl C, Runswick S, Conte P. Olaparib for Metastatic Breast Cancer in Patients with a Germline BRCA Mutation. N Engl J Med. 2017 Aug. 10; 377(6):523-533

Stathis A, Zucca E, Bekradda M, Gomez-Roca C, Delord J P, de La Motte Rouge T, Uro-Coste E, de Braud F, Pelosi G, French C A. Clinical Response of Carcinomas Harboring the BRD4-NUT Oncoprotein to the Targeted Bromodomain Inhibitor OTX015/MK-8628. Cancer Discov. 2016 May; 6(5):492-500

EXAMPLES

Tissue culture media and reagents were obtained from ThermoFisher Scientific. Talazoparib, olaparib, niraparib, and veliparib were obtained from Selleck Chemicals.

Example 1: Synthesis of Compound I

Step A: Synthesis of 5-bromo-N³-(phenylmethylene)pyridine-2,3-diamine (Compound B)

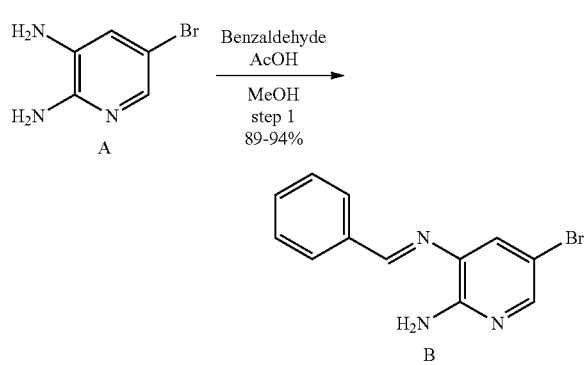

Starting material A was dissolved in methanol and acetic acid. The solution was cooled to 0-5° C. and benzaldehyde was added dropwise. Once the reaction was complete, process water and a NaHCO₃ solution was added dropwise, keeping the temperature low (0-5° C.). The solid was filtered off and washed with methanol/water 1:1, followed by drying, leaving Compound B in 94% yield and +99% purity by HPLC. 1H-NMR (DMSO-$d_6$): δ 8.75 (1H), 8.04 (2H), 7.93 (1H), 7.65 (1H), 7.50-7.60 (3H).

Step B: Synthesis of N³-benzyl-5-bromopyridine-2,3-diamine (Compound C)

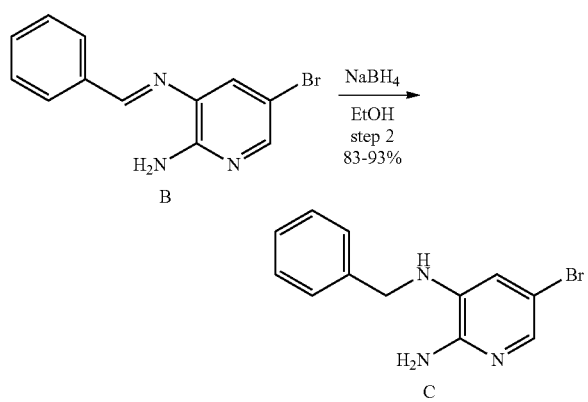

Compound B was dissolved in ethanol and NaHB₄ was added in portions keeping the temperature between 15-25° C. The reaction mixture was stirred for 8-15 h until the reaction was complete as monitored by HPLC. A HCl solution was added, adjusting pH to 6-7, followed by process water, keeping the temperature between 15-25° C. The mixture was stirred for 1-5 h, filtered and washed with an ethanol/water mixture. Following drying at ~60° C. for 15-20 h, Compound C was obtained. ¹H-NMR (DMSO-$d_6$): δ 7.2-7.4 (6H), 6.55 (1H), 5.70-5.83 (3H), 4.30 (2H).

Step C: Synthesis of N³-benzyl-5-(3,5-dimethyl-1,2-oxazol-4-yl)pyridine-2,3-diamine (Compound D)

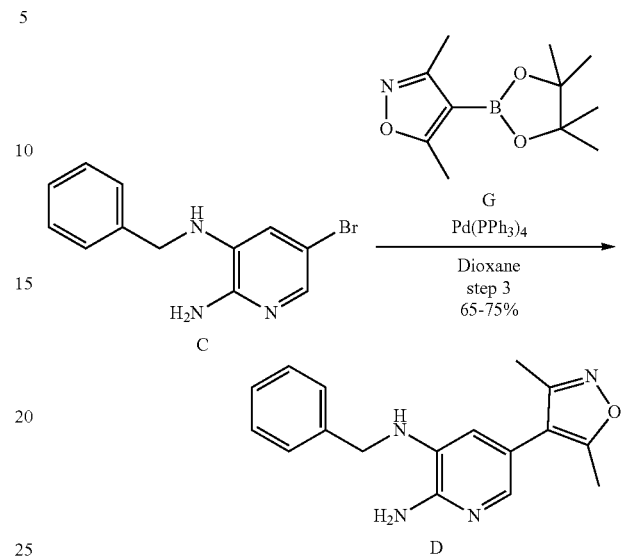

Compound C, Compound G, and potassium phosphate tribasic trihydrate were mixed followed by addition of 1,4-Dioxane and process water. The resulting mixture was thoroughly purged with nitrogen. Tetrakis(triphenylphosphine)palladium(0) was added and the mixture was heated to ≥90° C. until the ratio of Compound C to Compound D was not more than 1%. After cooling, the reaction mixture was filtered, the solid washed with 1,4-dioxane and then concentrated. Process water was added and the mixture was stirred until the amount of Compound D remaining in the mother liquors was not more than 0.5%. Compound D was isolated by filtration and sequentially washed with 1,4-dioxane/water and t-butylmethyl ether. The wet cake was mixed in methylene chloride and silica gel. After stirring, the mixture was filtered then concentrated. The mixture was cooled and t-butylmethyl ether was added. The product was isolated by filtration and dried until the methylene chloride, t-butylmethyl ether, and moisture levels are not more than 0.5%. ¹H-NMR (DMSO-$d_6$): δ 7.30-7.45 (4H), 7.20-7.25 (2H), 6.35 (1H), 5.65-5.80 (3H), 4.30-4.40 (2H), 2.15 (3H), 1.95 (3H).

Step D: Synthesis of 1-benzyl-6-(3,5-dimethyl-1,2-oxazol-4-yl)-3H-imidazo[4,5-b]pyridin-2-one (Compound E)

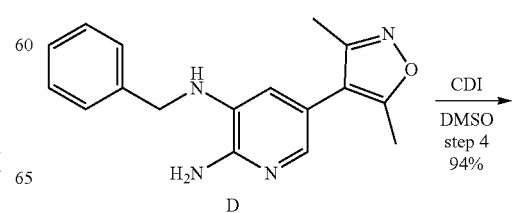

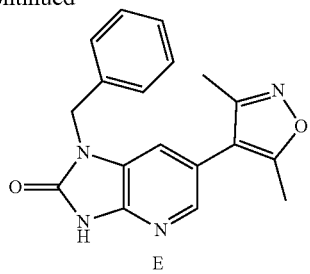

E

Carbonyldiimidazole solid was added to a stirring mixture of Compound D and dimethylsulfoxide. The mixture was heated until the ratio of Compound D to Compound E was NMT 0.5%. The mixture was cooled and process water was added over several hours. The resulting mixture was stirred at ambient temperature for at least 2 h. The product was isolated by filtration and washed with process water. The dimethylsulfoxide was verified to be NMT 0.5% before drying using heat and vacuum. Drying was complete when the moisture level was NMT 0.5%, leaving Compound E. $^1$H-NMR (DMSO-d$_6$): δ 11.85 (1H), 7.90 (1H), 7.20-7.45 (6H), 5.05 (2H), 3.57 (3H), 2.35 (3H), 2.15 (3H).

Step E: Synthesis of 4-[1-benzyl-2-chloro-1H-imidazo[4,5-b]pyridine-6-yl]-3,5-dimethyl-1,2-oxazole (Compound F)

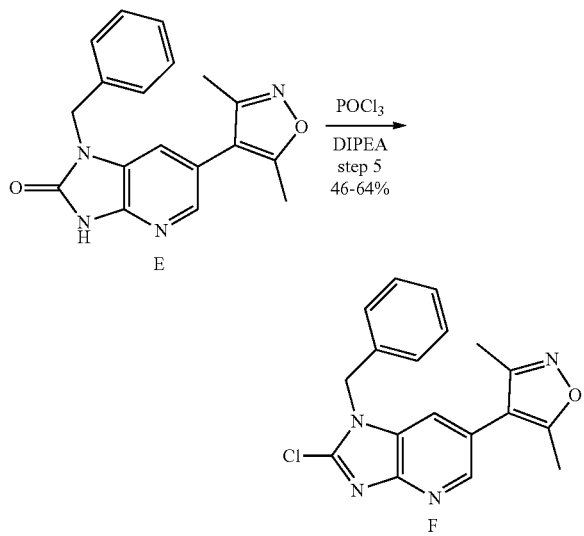

Compound E and phosphorus oxychloride were mixed and then treated with diisopropylethyl amine (DIPEA), which can be added dropwise. The resulting mixture was heated for several hours, cooled, and sampled for reaction completion. If the ratio of Compound E to Compound F was not more than 0.5% then the reaction was complete. Otherwise, the reaction was heated for additional time and sampled as before. After the reaction was complete, the mixture was concentrated then cooled. Ethyl acetate was added and the mixture was concentrated under vacuum several times. Ethyl acetate (EtOAc) was added to the concentrate, the mixture was cooled and then added to aqueous sodium bicarbonate. The organic phase was separated and the organic layer was washed with aqueous sodium bicarbonate and then water. The organic phase was concentrated, ethyl acetate was added, and the mixture was concentrated to assure that the moisture level was not more than 0.2%. The mixture in ethyl acetate was decolorized with carbon. The mixture was concentrated and n-heptane was added. The product was isolated by filtration and dried under vacuum. Drying was complete when residual moisture, ethyl acetate, and n-heptane were not more than 0.5%. $^1$H-NMR (MeOH-d$_4$): δ 8.40 (1H), 7.90 (1H), 7.25-7.45 (5H), 5.65 (2H), 2.37 (3H), 2.22 (3H).

Step F: Synthesis of 1-benzyl-6-(3,5-dimethyl-1,2-oxazol-4-yl)-N-methyl-1H-imidazo[4,5-b]pyridine-2-amine (Compound 1)

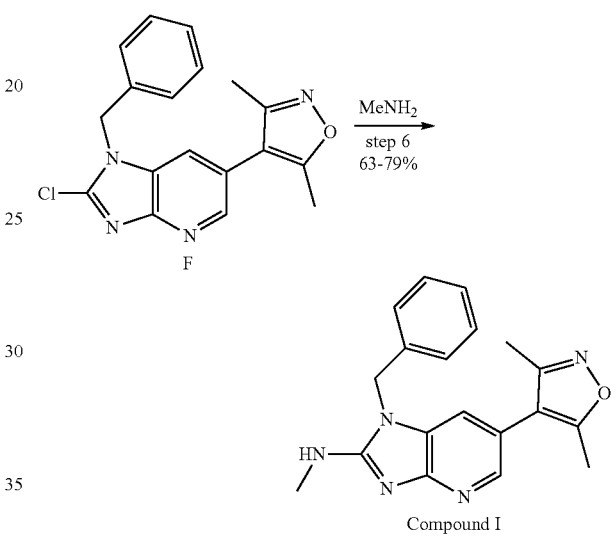

Compound F was mixed with methylamine in tetrahydrofuran (THF) and stirred at ambient temperature until the ratio of Compound F to Compound I was NMT 0.1% by HPLC. After reaction completion, the mixture was concentrated under vacuum, process water added, and the product isolated by filtration. The filter cake was washed with process water. The wet cake was dissolved in hydrochloric acid and the resulting solution was washed with methylene chloride to remove impurities. The aqueous solution was neutralized with a sodium hydroxide solution and Compound I was isolated by filtration, washed with process water, and dried under vacuum. If necessary, to remove any remaining hydrochloric acid, the dried material can be dissolved in ethanol, treated with a solution of sodium hydroxide in ethanol, followed by addition of process water to precipitate the product. Compound I was isolated by filtration, washed with process water, and dried. 1H-NMR (DMSO-d$_6$): δ 7.96 (d, 1H, J=2.0 Hz), 7.42 (d, 1H, J=2.0 Hz), 7.37 (q, 1H, J=4.2 Hz), 7.32 (m, 2H), 7.26 (m, 1H), 7.24 (m, 2H), 5.30 (s, 2H), 3.00 (d, 3H, 4.5 Hz), 2.34 (s, 3H), 2.16 (s, 3H). $^{13}$C-NMR (DMSO-d$_6$): δ 164.8, 158.4, 157.7, 156.0, 141.1, 136.4, 128.6 (2C), 127.5, 127.4, 127.2 (2C), 115.8, 114.2 (2C), 44.5, 29.3, 11.2, 10.3.

Example 2: Crystalline Mesylate of Compound I

About 5 g of Compound I was dissolved in ethanol (115 mL) and a solution of methanesulfonic acid in ethanol (10 mL, 158.7 mg/mL) was added, according to a 1:1 molar ratio. The mixture was shaken at 50° C. for 2 h before concentrated to half volume and stirred overnight. The formed solid (mesylate salt/co-crystal of Compound I Form 1) was isolated, dried, and characterized.

The mesylate salt/co crystal of Compound I Form I was also obtained from other solvents and solvent mixtures, including acetone and acetonitrile.

Figure 9:
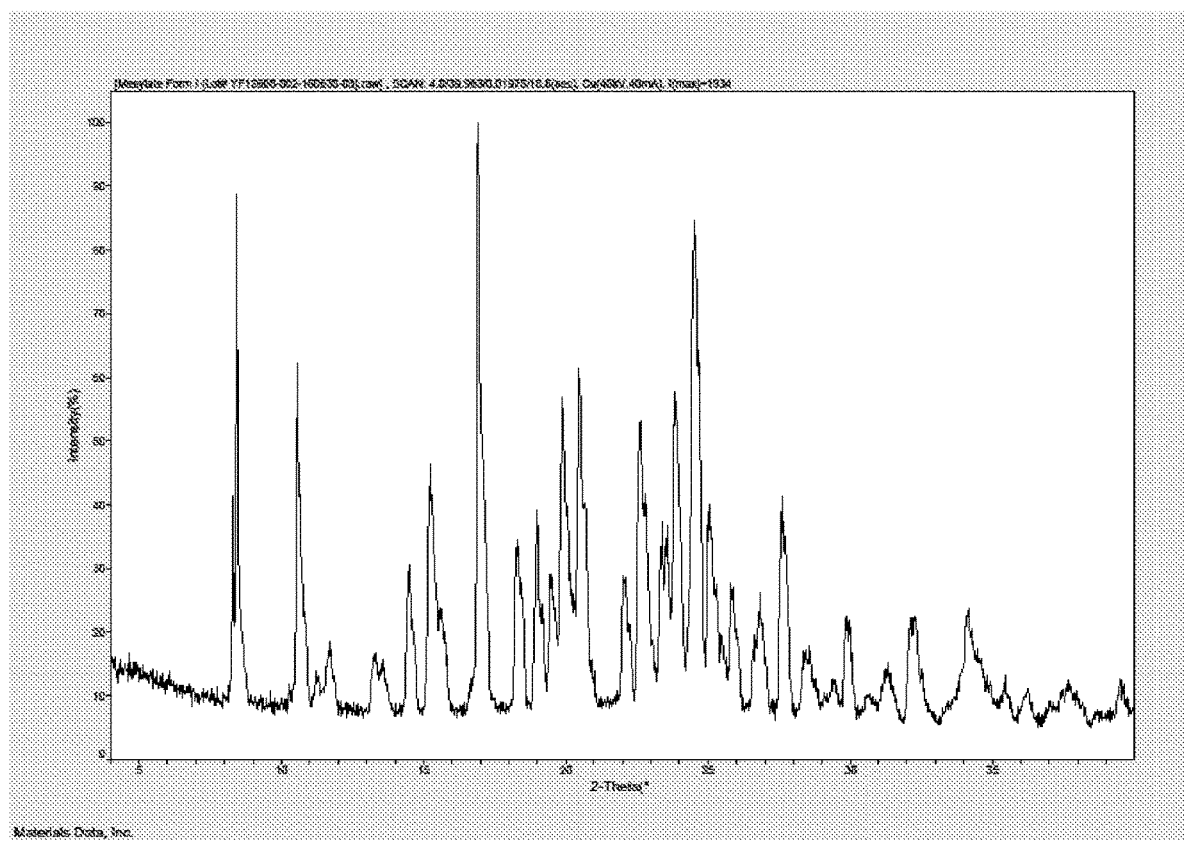
FIG. 9 shows an X-ray powder diffractogram (XRPD) of a mesylate salt/co-crystal of Compound I.

The mesylate salt/co crystal of Compound I Form I was characterized by XRPD comprising the following peaks, in terms of 2-theta, at 8.4±0.2, 10.6±0.2, 11.7±0.2, 14.5±0.2, 15.3±0.2, 16.9±0.2, 18.2±0.2, 19.0±0.2, 19.9±0.2, 20.5±0.2, 22.6±0.2, 23.8±0.2, 24.5±0.2, and 27.6±0.2 degrees, as determined on a diffractometer using Cu—$K_\alpha$ radiation tube (FIG. 9).

The mesylate salt/co crystal of Compound I Form I was characterized by DSC having an endothermic peak at a temperature of about 207° C. (FIG. 10).

Figure 10:
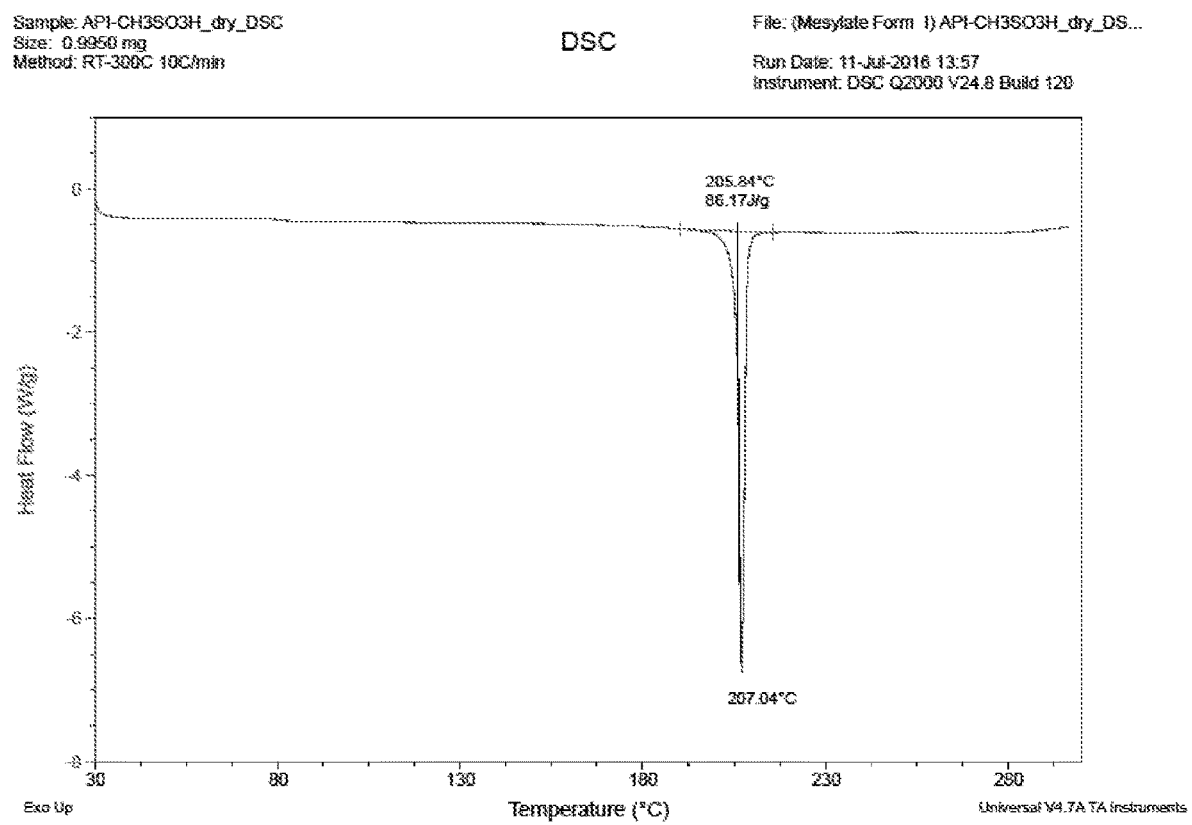
FIG. 10 shows a differential scanning calorimeter (DSC) curve of a mesylate salt/co-crystal of Compound I.
Figure 11:
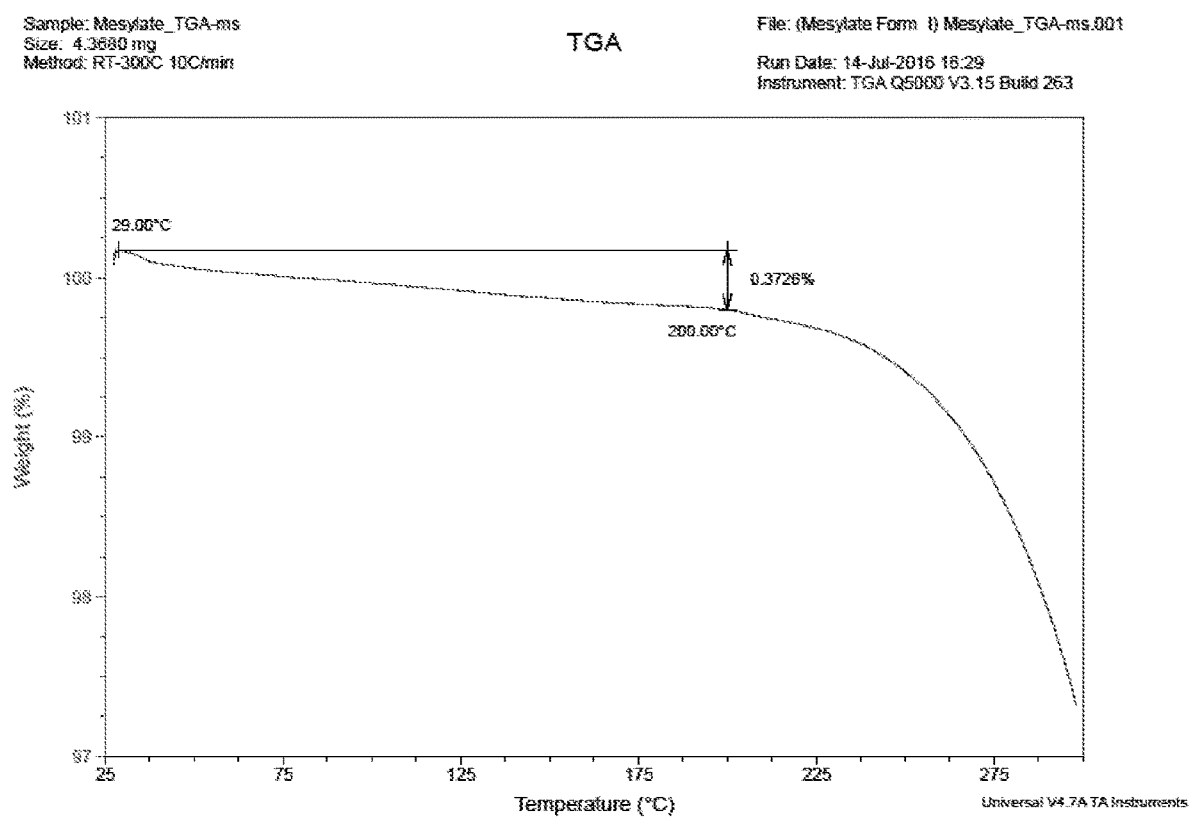
FIG. 11 shows a thermogravimetric analysis (TGA) of a mesylate salt/co-crystal of Compound I.

The mesylate salt/co crystal of Compound I Form I was characterized by TGA, having a thermogram as shown in FIG. 10, confirming that Compound I Form I is an anhydrous form.

Example 3: Compound I and Talazoparib in HCC1937 (BRCA1 Mutant) Cells

Synergistic Inhibition of HCC1937 Cell Viability by Combination of Compound I with Talazoparib HCC1937 cells (CRL-2336) were plated at a density of 1,000 cells per well in 96 well flat bottom plates in RPMI-1640 media containing 10% FBS and penicillin/streptomycin and incubated for 24 hours at 37° C., 5% $CO_2$. Media was replaced with RPM1-1640 media containing 10% FBS with varying doses of either Compound I or talazoparib as single agents, or a combination of both drugs, and incubated at 37° C., 5% $CO_2$ for 7 days. Triplicate wells were used for each concentration and wells containing only media with 0.1% DMSO were used as a control. To measure cell viability, 100 uL of a 1:100 dilution of GF-AFC substrate into the Assay Buffer (CellTiter Fluor Cell Viability Assay (Promega)) were added to each well and incubated at 37° C., 5% $CO_2$ for an additional 30-90 minutes. Fluorescence at 380-400 nm Excitation/505 nm Emission was read in a fluorometer and the percentage of cell titer relative to DMSO-treated cells was calculated after correcting for background by subtracting the blank well's signal. IC50 values for single agents were calculated using the GraphPad Prism software. Quantification of synergy was done by calculating combination indices (CI) using the CalcuSyn software (Biosoft) based on the Chou-Talalay algorithm (Chou and Talalay, 1984), and averaging the CI values for the effective doses (ED) 50, 75, and 90. As shown in FIG. 1, addition of Compound I to talazoparib resulted in improved inhibition of cell viability compared to either single agent with an average CI value of 0.5.

Example 4: Compound I and Olaparib in HCC1937 (BRCA1 Mutant) Cells

Figure 2:
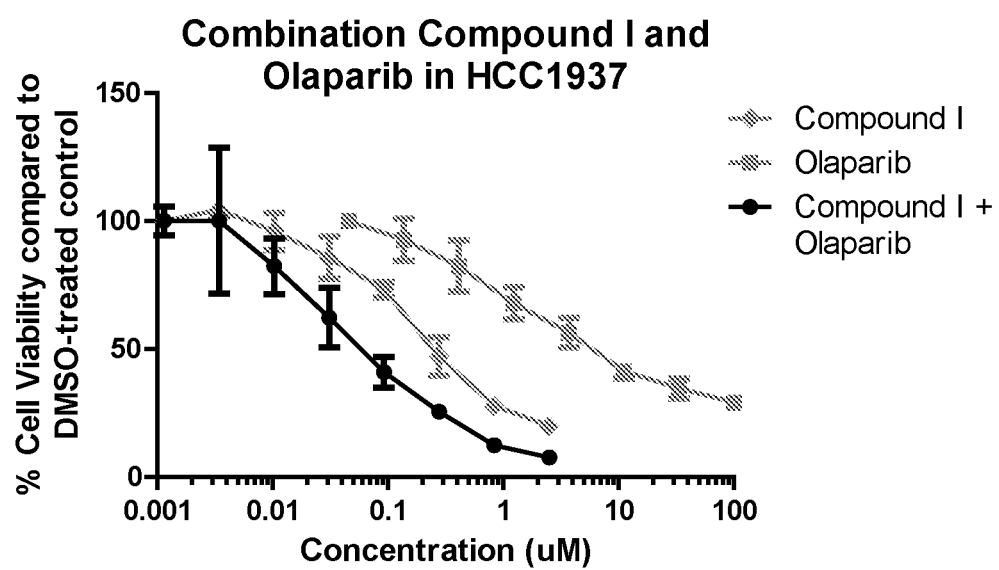
FIG. 2 shows the effect of Compound I, olaparib, and the combination of Compound I and olaparib on cell viability of TNBC HCC1937 cells (mutant BRCA1).

Synergistic Inhibition of HCC1937 Cell Viability by Combination of Compound I with Olaparib HCC1937 cells (CRL-2336) were plated at a density of 1,000 cells per well in 96 well flat bottom plates in RPMI-1640 media containing 10% FBS and penicillin/streptomycin and incubated for 24 hours at 37° C., 5% $CO_2$. Media was replaced with RPM1-1640 media containing 10% FBS with varying doses of either Compound I or olaparib as single agents, or a combination of both drugs, and incubated at 37° C., 5% $CO_2$ for 7 days. The cells were retreated as described above on the $3^{rd}$ or $4^{th}$ day. Triplicate wells were used for each concentration and wells containing only media with 0.1% DMSO were used as a control. To measure cell viability, 100 uL of a 1:100 dilution of GF-AFC substrate into the Assay Buffer (CellTiter Fluor Cell Viability Assay (Promega)) were added to each well and incubated at 37° C., 5% $CO_2$ for an additional 30-90 minutes. Fluorescence at 380-400 nm Excitation/505 nm Emission was read in a fluorometer and the percentage of cell titer relative to DMSO-treated cells was calculated after correcting for background by subtracting the blank well's signal. IC50 values for single agents were calculated using the GraphPad Prism software. Quantification of synergy was done by calculating combination indices (CI) using the CalcuSyn software (Biosoft) based on the Chou-Talalay algorithm (Chou and Talalay, 1984), and averaging the CI values for the effective doses (ED) 50, 75, and 90. As shown in FIG. 2, addition of Compound I to olaparib resulted in improved inhibition of cell viability compared to either single agent with an average CI value of 0.4.

Example 5: Compound I and Veliparib in HCC1937 (BRCA1 Mutant) Cells

Figure 3:
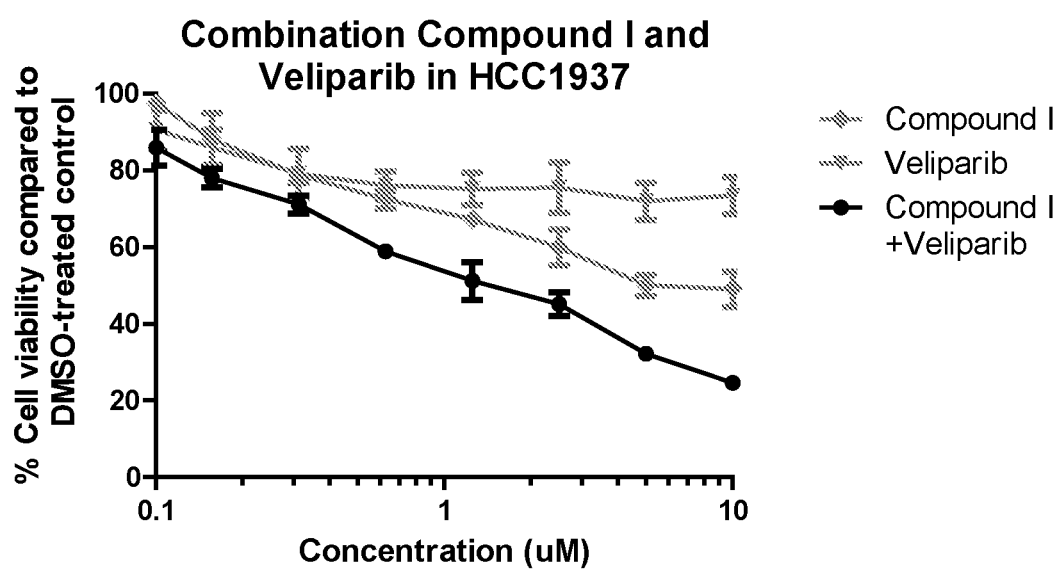
FIG. 3 shows the effect of Compound I, veliparib, and the combination of Compound I and veliparib on cell viability of TNBC cell line HCC1937 (BRCA1 mutant).

Synergistic Inhibition of HCC1937 Cell Viability by Combination of Compound I with Veliparib HCC1937 cells (CRL-2336) were plated at a density of 10,000 cells per well in 96 well flat bottom plates in RPMI-1640 media containing 10% FBS and penicillin/streptomycin and incubated for 24 hours at 37° C., 5% $CO_2$. Media was replaced with RPM1-1640 media containing 10% FBS with varying doses of either Compound I or veliparib as single agents, or a combination of both drugs, and incubated at 37° C., 5% $CO_2$ for 7 days. The cells were retreated as described above on the $3^{rd}$ or $4^{th}$ day. Triplicate wells were used for each concentration and wells containing only media with 0.1% DMSO were used as a control. To measure cell viability, 100 uL of a 1:100 dilution of GF-AFC substrate into the Assay Buffer (CellTiter Fluor Cell Viability Assay (Promega)) were added to each well and incubated at 37° C., 5% $CO_2$ for an additional 30-90 minutes. Fluorescence at 380-400 nm Excitation/505 nm Emission was read in a fluorometer and the percentage of cell titer relative to DMSO-treated cells was calculated after correcting for background by subtracting the blank well's signal. IC50 values for single agents were calculated using the GraphPad Prism software. Quantification of synergy was done by calculating combination indices (CI) using the CalcuSyn software (Biosoft) based on the Chou-Talalay algorithm (Chou and Talalay, 1984), and averaging the CI values for the effective doses (ED) 50, 75, and 90. As shown in FIG. 3, addition of Compound I to veliparib resulted in improved inhibition of cell viability compared to either single agent with an average CI value of 0.1.

Example 6: Compound I and Olaparib in HCC1599 (BRCA2 Mutant) Cells

Figure 4:
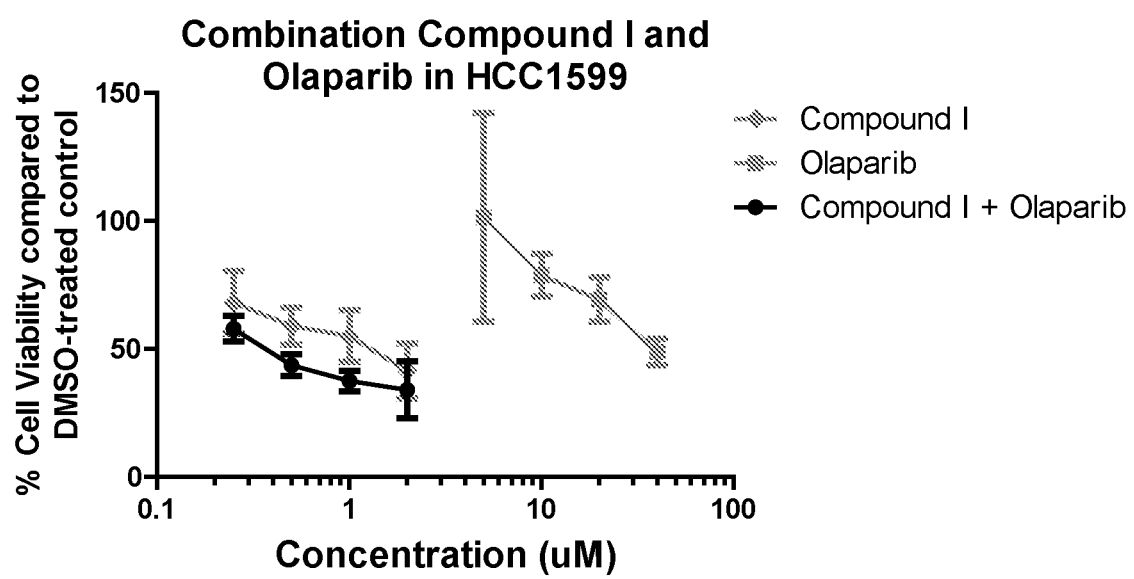
FIG. 4 shows the effect of Compound I, olaparib, and the combination of Compound I and olaparib on cell viability of TNBC HCC1599 cells (mutant BRCA2).

Confluent HCC1599 cells (CRL-2331) were diluted 1:2 and plated 50 uL/well in 96 well flat bottom plates in RPM1-1640 media containing 10% FBS and penicillin/streptomycin. 50 uL/well of media with RPMI-1640—containing 10% FBS with varying doses of either Compound I or olaparib as single agents, or a combination of both drugs, was added to the cells and incubated at 37° C., 5% $CO_2$ for 3 days. Triplicate wells were used for each concentration and wells containing only media with 0.2% DMSO were used as a control. To measure cell viability, 20 uL of an MTS tetrazolium compound (CellTiter 96® AQueous One Solution Cell Proliferation Assay (Promega)) was added to each well and incubated at 37° C., 5% $CO_2$ for an additional 3 hours. The absorbance at 490 nm was read using a 96-well plate reader (MultiSkan GO) and the percentage of cell titer relative to DMSO-treated cells was calculated after correcting for background by subtracting the blank well's signal. IC50 values for single agents were calculated using the GraphPad Prism software. Quantification of synergy was done by calculating combination indices (CI) using the CalcuSyn software (Biosoft) based on the Chou-Talalay algorithm (Chou and Talalay, 1984), and averaging the CI values for the effective doses (ED) 50, 75, and 90. As shown in FIG. 4, addition of Compound I to olaparib resulted in improved inhibition of cell viability compared to either single agent.

Example 7: Compound I and Talazoparib in BT549 (BRCA1/2 Wild-Type) Cells

Figure 5:
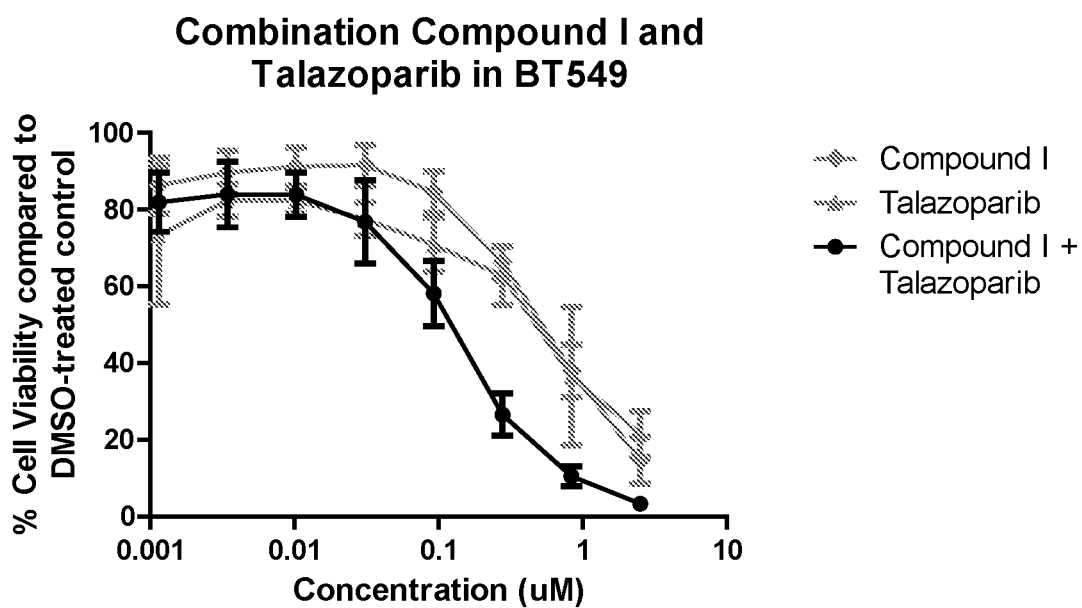
FIG. 5 shows the effect of Compound I, talazoparib, and the combination of Compound I and talazoparib on cell viability of TNBC BT549 cells (wild-type BRCA1 and BRCA2).

Synergistic Inhibition of BT549 Cell Viability by Combination of Compound I with Talazoparib BT-549 cells (HTB-122) were plated at a density of 1,000 cells per well in 96 well flat bottom plates in RPMI-1640 media containing 10% FBS, 0.023 IU/mL insulin, and penicillin/streptomycin and incubated for 24 hours at 37° C., 5% $CO_2$. Media was replaced with RPMI-1640 media containing 10% FBS, 0.023 IU/mL insulin, with varying doses of either Compound I or talazoparib as single agents, or a combination of both drugs, and incubated at 37° C., 5% $CO_2$ for 7 days. The cells were retreated as described above on the $3^{rd}$ or $4^{th}$ day. Triplicate wells were used for each concentration and wells containing only media with 0.1% DMSO were used as a control. To measure cell viability, 100 uL of a 1:100 dilution of GF-AFC substrate into the Assay Buffer (CellTiter Fluor Cell Viability Assay (Promega)) were added to each well and incubated at 37° C., 5% $CO_2$ for an additional 30-90 minutes. Fluorescence at 380-400 nm Excitation/505 nm Emission was read in a fluorometer and the percentage of cell titer relative to DMSO-treated cells was calculated after correcting for background by subtracting the blank well's signal. IC50 values for single agents were calculated using the GraphPad Prism software. Quantification of synergy was done by calculating combination indices (CI) using the CalcuSyn software (Biosoft) based on the Chou-Talalay algorithm (Chou and Talalay, 1984), and averaging the CI values for the effective doses (ED) 50, 75, and 90. As shown in FIG. 5, addition of Compound I to talazoparib resulted in improved inhibition of cell viability compared to either single agent with an average CI value of 0.2.

Example 8: Compound I and Veliparib in BT549 (BRCA1/2 Wild-Type) Cells

Figure 6:
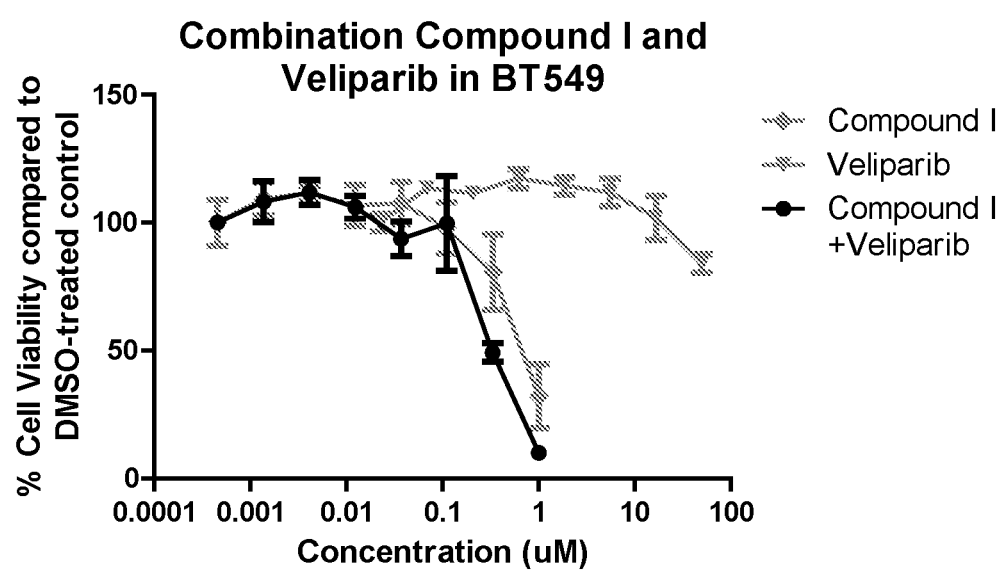
FIG. 6 shows the effect of Compound I, veliparib, and the combination of Compound I and veliparib on cell viability of TNBC BT549 cells (wild-type BRCA1 and BRCA2).

Synergistic Inhibition of BT549 Cell Viability by Combination of Compound I with Veliparib BT-549 cells (HTB-122) were plated at a density of 1,000 cells per well in 96 well flat bottom plates in RPMI-1640 media containing 10% FBS, 0.023 IU/mL insulin, and penicillin/streptomycin and incubated for 24 hours at 37° C., 5% $CO_2$. Media was replaced with RPMI-1640 media containing 10% FBS, 0.023 IU/mL insulin, with varying doses of either Compound I or olaparib as single agents, or a combination of both drugs, and incubated at 37° C., 5% $CO_2$ for 7 days. The cells were retreated as described above on the $3^{rd}$ or $4^{th}$ day. Triplicate wells were used for each concentration and wells containing only media with 0.1% DMSO were used as a control. To measure cell viability, 100 uL of a 1:100 dilution of GF-AFC substrate into the Assay Buffer (CellTiter Fluor Cell Viability Assay (Promega)) were added to each well and incubated at 37° C., 5% $CO_2$ for an additional 30-90 minutes. Fluorescence at 380-400 nm Excitation/505 nm Emission was read in a fluorometer and the percentage of cell titer relative to DMSO-treated cells was calculated after correcting for background by subtracting the blank well's signal. IC50 values for single agents were calculated using the GraphPad Prism software. Quantification of synergy was done by calculating combination indices (CI) using the CalcuSyn software (Biosoft) based on the Chou-Talalay algorithm (Chou and Talalay, 1984), and averaging the CI values for the effective doses (ED) 50, 75, and 90. As shown in FIG. 6, addition of Compound I to veliparib resulted in improved inhibition of cell viability compared to either single agent with an average CI value of 0.2.

Example 9: Compound I and Olaparib in BT549 (BRCA1/2 Wild-Type) Cells

Figure 7:
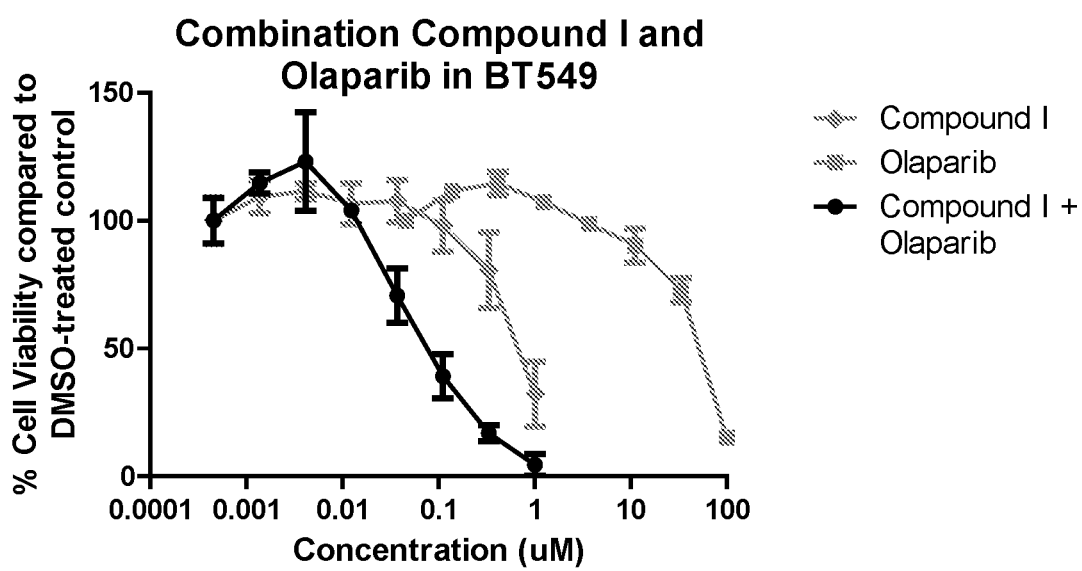
FIG. 7 shows the effect of Compound I, olaparib, and the combination of Compound I and olaparib on cell viability of TNBC BT549 cells (wild-type BRCA1 and BRCA2).

Synergistic Inhibition of BT549 Cell Viability by Combination of Compound I with Olaparibb BT-549 cells (HTB-122) were plated at a density of 1,000 cells per well in 96 well flat bottom plates in RPMI-1640 media containing 10% FBS, 0.023 IU/mL insulin, and penicillin/streptomycin and incubated for 24 hours at 37° C., 5% $CO_2$. Media was replaced with RPMI-1640 media containing 10% FBS, 0.023 IU/mL insulin, with varying doses of either Compound I or veliparib as single agents, or a combination of both drugs, and incubated at 37° C., 5% $CO_2$ for 7 days. The cells were retreated as described above on the $3^{rd}$ or $4^{th}$ day. Triplicate wells were used for each concentration and wells containing only media with 0.1% DMSO were used as a control. To measure cell viability, 100 uL of a 1:100 dilution of GF-AFC substrate into the Assay Buffer (CellTiter Fluor Cell Viability Assay (Promega)) were added to each well and incubated at 37° C., 5% $CO_2$ for an additional 30-90 minutes. Fluorescence at 380-400 nm Excitation/505 nm Emission was read in a fluorometer and the percentage of cell titer relative to DMSO-treated cells was calculated after correcting for background by subtracting the blank well's signal. IC50 values for single agents were calculated using the GraphPad Prism software. Quantification of synergy was done by calculating combination indices (CI) using the CalcuSyn software (Biosoft) based on the Chou-Talalay algorithm (Chou and Talalay, 1984), and averaging the CI values for the effective doses (ED) 50, 75, and 90. As shown in FIG. 7, addition of Compound I to olaparib resulted in improved inhibition of cell viability compared to either single agent with an average CI value of 0.2.

Example 10: Compound I and Niraparib in HCC-70 (BRCA1/2 Wild Type Cells)

Figure 8:
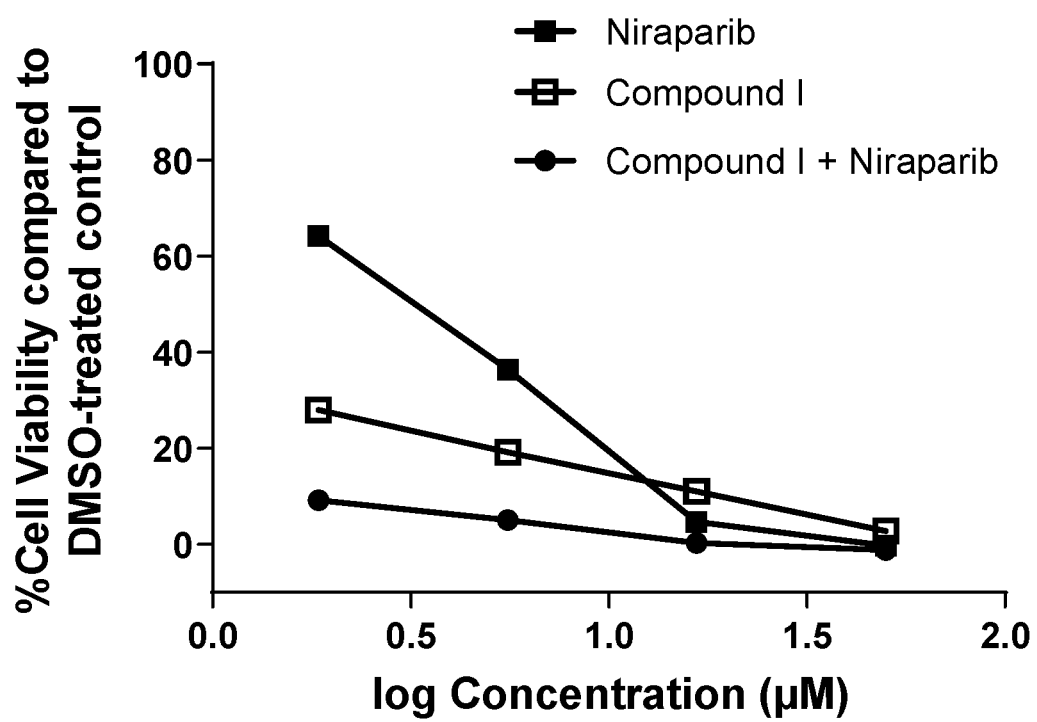
FIG. 8 shows the effect of Compound I, niraparib, and the combination of Compound I and niraparib on cell viability of HCC-70 cells (wild-type BRCA-1 and BRCA-2).

Synergistic Inhibition of HCC-70 Cell Viability by Combination of Compound I with Niraparib HCC-70 cells were plated at a density of 2,500 cells per well in 96 well flat bottom plates in 1640-RPMI media containing 10% FBS and penicillin/streptomycin and incubated for 24 hours at 37° C., 5% $CO_2$. Media was replaced with 1640-RPMI containing 10% FBS with constant ratios of either Compound I or niraparib as single agents, or a combination of both drugs at four different concentrations (2×IC50, 1×IC50, 0.5×IC50, 0.25×IC50), and incubated at 37° C., 5% $CO_2$ for 7 days. The cells were retreated as described above on the 3-d or 4-th day. Triplicate wells were used for each concentration and wells containing only media with 0.1% DMSO were used as a control. To measure cell viability, 100 uL of a 1:100 dilution of GF-AFC substrate into the Assay Buffer (CellTiter Fluor Cell Viability Assay (Promega)) were added to each well and incubated at 37° C., 5% $CO_2$ for an additional 30-90 minutes. Fluorescence at 380-400 nm Excitation/505 nm Emission was read in a fluorometer and the percentage of cell titer relative to DMSO-treated cells was calculated after correcting for background by subtracting the blank well's signal. IC50 values for single agents were calculated using the GraphPad Prism software. Quantification of synergy was done by calculating combination indices (CI) using the CalcuSyn software (Biosoft) based on the Chou-Talalay algorithm (Chou and Talalay, 1984), and averaging the CI values for the effective doses (ED) 50, 75, and 90. As shown in FIG. 8 addition of Compound I to niraparib resulted in improved inhibition of cell viability compared to either single agent with an average CI value of 0.2-0.4.

Example 11: Clinical Development

Part 1 may be an open label, non-randomized, dose escalation of Compound I in combination with talazoparib in patients with TNBC without germline BRCA1/2 mutations, with the objective to evaluate safety, pharmacokinetics, and activity. A standard 3+3 cohort design will be utilized. Cohorts of up to 6 patients will be enrolled at each dose level, and each patient will participate in only one cohort. Each cycle will be 28 days in duration. Dose escalation will continue after all patients enrolled within a cohort have completed the 28 day Cycle 1 DLT observation period. Toxicity will be graded and recorded according to the National Cancer Institute Common Terminology Criteria for Adverse Events (NCI CTCAE), Version 5.0. A DLT is defined as a clinically significant AE or laboratory abnormality that is considered possibly, probably or definitely related to study drug and which meets any of the following criteria:
  Grade 3 or greater non-hematologic clinical toxicity with the exception of Grade 3 nausea or Grade 3/4 vomiting or diarrhea unless persisting more than 72 hours despite maximal medical therapy. An increase of at least 2 grades in severity for fatigue present at baseline.
  Grade 4 anemia. Grade 4 neutropenia lasting more than 5 days. Grade 3 or greater febrile neutropenia (temperature≥38.5° C.). Grade 4 thrombocytopenia or Grade 3 thrombocytopenia with clinically significant bleeding, or any requirement for platelet transfusion. Any other Grade 3 or 4 laboratory abnormality that requires hospitalization
An ALT>3×ULN with concomitant total bilirubin>2×ULN. Any toxicity that results in more than 25% of missed doses during Cycle 1 of treatment. Definition of the Maximum Tolerated Dose: The MTD is defined as the highest dose level of Compound 1 in combination with talazoparib at which no more than 1 of 6 patients experiences a DLT during the first cycle of therapy.
  Part 2: Simon 2-Stage: Stage 1: Once a recommended dose of Compound I in combination with talazoparib has been determined in the dose escalation part of the study, 17 patients will be enrolled in Stage 1 of a Simon 2-Stage design for evaluation of objective response (complete response (CR), partial response (PR), or stable disease (SD) for ≥4 cycles) by RECIST 1.1. If there are ≥4 objective responses the study will proceed to Stage 2. The patient population in the Simon 2-stage is the same as the dose escalation patient population.
  Stage 2: If at least 4 patients in Stage 1 have an objective response (CR, PR or SD for ≥4 cycles) by RECIST 1.1, 20 patients will be enrolled in Stage 2 of the Simon 2-Stage design. Patients will receive daily recommended doses of Compound I in combination with talazoparib. Patients may continue receiving Compound I in combination with talazoparib until radiographic or clinical progression, unacceptable toxicity, requirement for non-protocol therapy or patient withdrawal from study.

Figure 12:
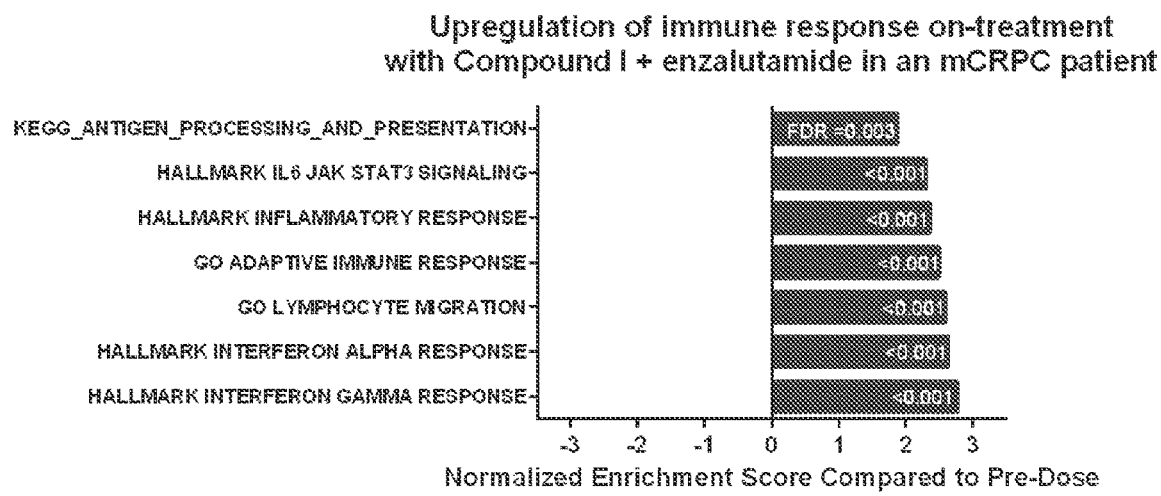
FIG. 12A shows the induction of the immune response in the tumor in response to the combination of Compound I with enzalutamide in mCRPC patients. Enzalutamide was continually present in both the pre-Compound I and post-Compound I sample.
FIG. 12B shows some of the immune response genes that were upregulated in the tumor.
Figure 12:
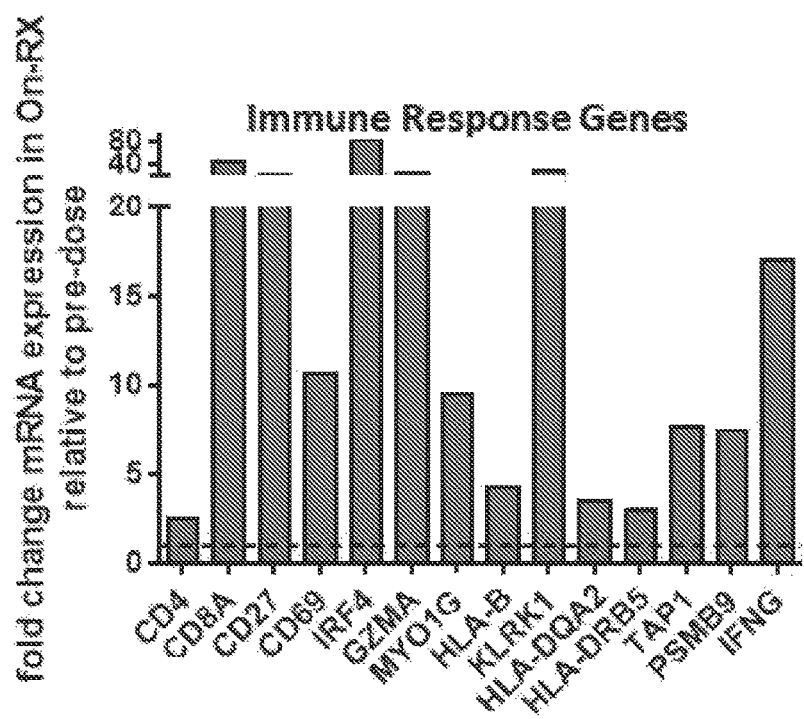

Example 12: Induction of the Immune Response and Interferon Gamma Signaling in the Tumor in Response to the Combination of Compound I with Enzalutamide in mCRPC Patients An mCRPC patient with prior progression on enzalutamide was dosed QD with Compound I while continuing enzalutamide. A tumor biopsy was obtained at screening (wherein patient is receiving enzalutamide only) and after 8 weeks of dosing with enzalutamide and Compound I. Whole transcriptome (RNA-Seq) analysis was done on the two biopsies and alignment was done using the STAR software, and differential gene expression analysis with Cufflinks using the BaseSpace™ Sequence Hub default parameters between December 2018 and August 2019. Additional independent analysis was done using the SALMON alignment software and BioConductor. Identification of differentially expressed gene signatures was done using geneset enrichment analysis (GSEA) using gene signatures from the Molecular Signature Database (Subramanian A, Tamayo P, et al. (2005, PNAS 102, 15545-15550); Liberzon A, et al. (2011, Bionformatics 27, 1739-1740); Liberzon A, et al. (2015, Cell Systems 1, 417-425). As shown in FIG. 12A, several immune-related signatures were significantly upregulated in the on-treatment biopsy. The relevant genesets are indicated in the figure and genes involved in each geneset can be downloaded from MSigDB. In FIG. 12B, some of the genes found in these genesets are graphed to show the extent of upregulation. Upregulation of genesets involved in adaptive immune response, antigen presentation, and interferon-gamma signaling suggests that the combination of Compound I and enzalutamide have induced an immunoresponsive phenotype. Given that PARP inhibitors have shown a potential to increase response to checkpoint inhibitors by upregulating the patient's immune response, it indicates that a combination of Compound I, a PARP inhibitor, and a checkpoint inhibitor could also increase responses in the context of breast cancer.

What is claimed is:
1. A method for treating a triple-negative breast cancer (TNBC) comprising administrating to a subject in need thereof a BET bromodomain inhibitor selected from 1-benzyl-6-(3,5-dimethylisoxazol-4-yl)-N-methyl-1H-imidazo[4,5-b]pyridin-2-amine (Compound I), 1-benzyl-6-(3,5-dimethylisoxazol-4-yl)-1H-imidazo[4,5-b]pyridin-2-amine, and pharmaceutically acceptable salts/co-crystals thereof, with a second therapeutic agent, wherein the second therapeutic agent is talazoparib.
2. The method according to claim 1, wherein the BET bromodomain inhibitor is Compound I.

3. The method according to claim 1, wherein the BET bromodomain inhibitor is the mesylate salt/co-crystal of Compound I Form I.

4. The method according to claim 1, further comprising administration of a checkpoint inhibitor.

5. The method according to claim 1, wherein the subject previously has been treated with a breast cancer therapy.

6. The method according to claim 5, wherein the breast cancer therapy is chemotherapy.

7. The method according to claim 5, wherein the breast cancer therapy is immunotherapy.

8. The method according to claim 1, wherein the subject previously has shown disease progression on treatment with a PARP inhibitor.

9. The method according to claim 1, wherein the subject is a human.

10. The method according to claim 1, wherein the subject with breast cancer has one or both germline mutations BRCA1 and BRCA2.

11. The method according to claim 1, wherein the subject with breast cancer does not carry germline mutations BRCA1 or BRCA2.

12. The method according to claim 1, wherein the subject with breast cancer has somatic mutations to either BRCA1 or BRCA2.

13. The method according to claim 1, wherein the subject with breast cancer has one or more somatic mutations to homologous recombination (HR) genes selected from ATM, CHEK2, NBN, PALB2, ATR, RAD51, RAD54, DSS1, RPA1, CHK1, FANCD2, FANCA, FANCC, FANCM, BARD1, RAD51C, RAD51D, RIF1, and BRIP1.

14. The method according to claim 1, wherein the subject with breast cancer has one or more germline mutations to homologous recombination (HR) genes selected from ATM, CHEK2, NBN, PALB2, ATR, RAD51, RAD54, DSS1, RPA1, CHK1, FANCD2, FANCA, FANCC, FANCM, BARD1, RAD51C, RAD51D, RIF1, and BRIP1.

15. The method according to claim 1, wherein the subject has a tumor characterized as homologous recombination (HR)-proficient.

16. The method according to claim 1, wherein the subject has a tumor characterized as homologous recombination deficient (HRD).

17. The method according to claim 1, wherein a compound selected from 1-benzyl-6-(3,5-dimethylisoxazol-4-yl)-N-methyl-1H-imidazo[4,5-b]pyridin-2-amine (Compound I) and 1-benzyl-6-(3,5-dimethylisoxazol-4-yl)-1H-imidazo[4,5-b]pyridin-2-amine and pharmaceutically acceptable salts or co-crystals thereof, is dosed with talazoparib without resulting in thrombocytopenia as a dose-limiting toxicity.

* * * * *